United States Patent [19]

Meyer

[11] Patent Number: 5,569,191
[45] Date of Patent: Oct. 29, 1996

[54] DEVICE FOR PREPARING A MEDICINAL SUBSTANCE SOLUTION, SUSPENSION OR EMULSION

[76] Inventor: Gabriel Meyer, Route la Dullive, CH - 1195 Dully, Switzerland

[21] Appl. No.: 256,668

[22] PCT Filed: Dec. 15, 1993

[86] PCT No.: PCT/CH93/00282

§ 371 Date: Jul. 19, 1994

§ 102(e) Date: Jul. 19, 1994

[87] PCT Pub. No.: WO94/13344

PCT Pub. Date: Jun. 23, 1994

[30] Foreign Application Priority Data

Dec. 15, 1992 [FR] France .................................. 9215072
Dec. 23, 1992 [FR] France .................................. 9215699

[51] Int. Cl.⁶ .................................................. A61M 37/00
[52] U.S. Cl. ............................... 604/82; 604/87; 604/88; 604/201
[58] Field of Search ................................ 604/82–88, 92, 604/201–203, 205, 232, 411–413, 416; 215/DIG. 8; 222/82, 83, 83.5

[56] References Cited

U.S. PATENT DOCUMENTS

| | | | |
|---|---|---|---|
| 3,542,023 | 11/1970 | Ogle | 604/88 |
| 3,659,602 | 5/1972 | Cloyd | 604/88 |
| 3,841,329 | 10/1974 | Killinger . | |
| 4,014,330 | 3/1977 | Genese | 604/88 |
| 4,180,070 | 12/1979 | Genese . | |
| 4,909,795 | 3/1990 | Gelabert . | |
| 4,994,029 | 2/1991 | Rohrbough | 604/88 |
| 5,122,117 | 6/1992 | Haber et al. | 604/201 |
| 5,171,220 | 12/1992 | Morimoto | 604/88 |
| 5,472,022 | 12/1995 | Michel et al. | 141/1 |
| 5,472,422 | 12/1995 | Ljungquist | 604/89 |

FOREIGN PATENT DOCUMENTS

| | | | |
|---|---|---|---|
| 0298067 | 10/1991 | European Pat. Off. . | |
| 2625981 | 7/1989 | France . | |
| 929108 | 5/1982 | U.S.S.R. | 604/88 |
| 1120897 | 7/1968 | United Kingdom . | |

Primary Examiner—John D. Yasko
Assistant Examiner—Laird J. Knights
Attorney, Agent, or Firm—Davis, Bujold & Streck, P.A.

[57] ABSTRACT

The invention concerns a device for the preparation of a medicinal solution from two components, one of which is in powder, lyophilisate or liquid form and the other a dilutant or a liquid solvent. These components respectively are charged in a rear container (11) and a front container (13), each of which has an opening closed off by a stopper-piston-dish, which is axially movable. Both these stopper-piston-dishes (19, 24) are connected by a conveyance shaft (15) adapted to ensure a rigid, tight and sterile coupling between the two stopper-piston-dishes (19, 24) when the device (10) is in a charging position, and to define a channel between both these containers (11, 13) when the device is in a position of use. The stopper-piston-dishes (19, 24) have a central zone provided with a slit (31, 33)m which is strongly compressed and closed in tight fashion when the device is in charging position, and which is open when one end of the conveyance shaft (15) is introduced therein, the device then being in the position of use. FIG. 1

12 Claims, 20 Drawing Sheets

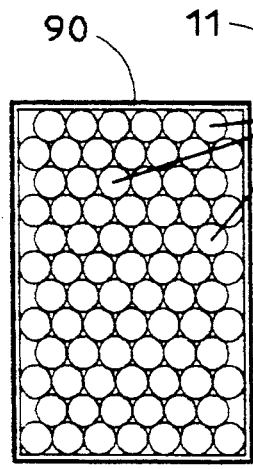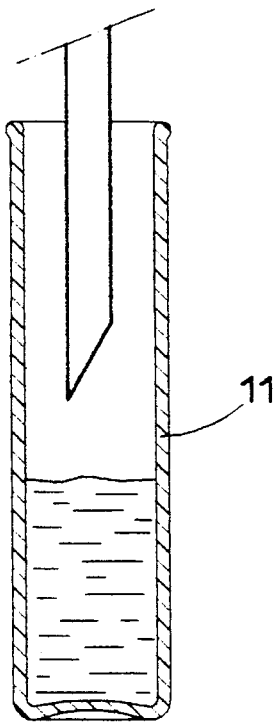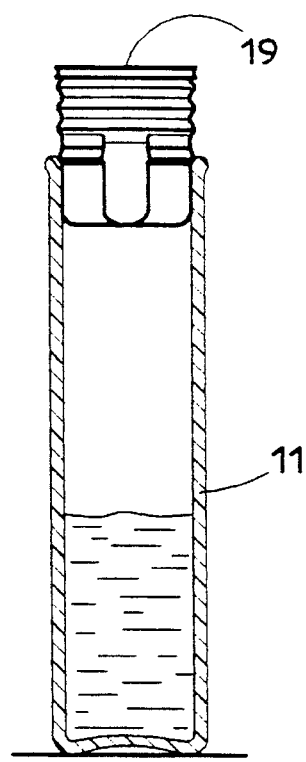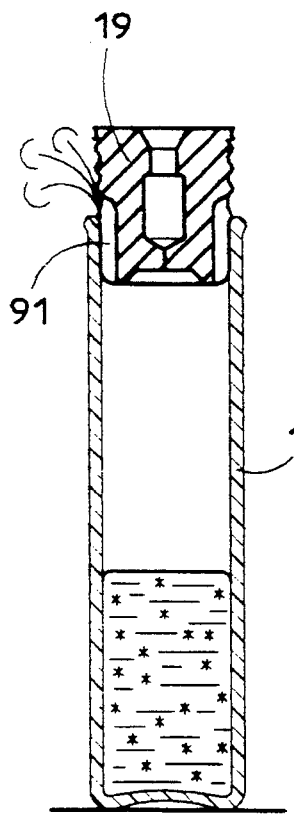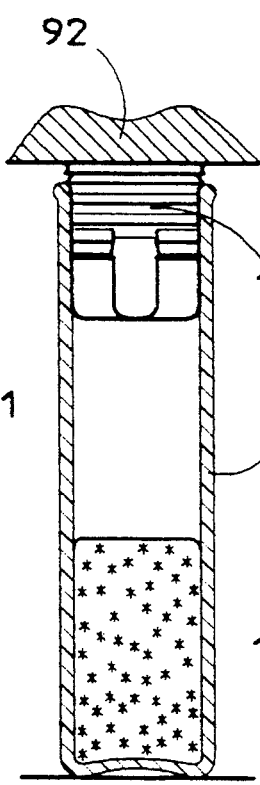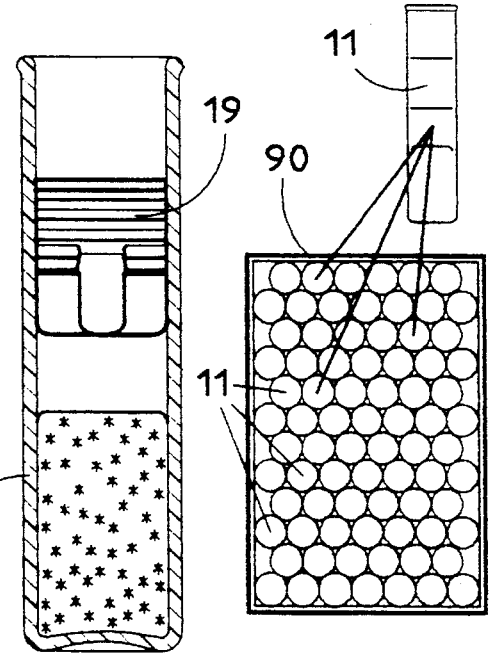
Fig.31  Fig.32  Fig.33  Fig.34  Fig.35  Fig.36  Fig.37

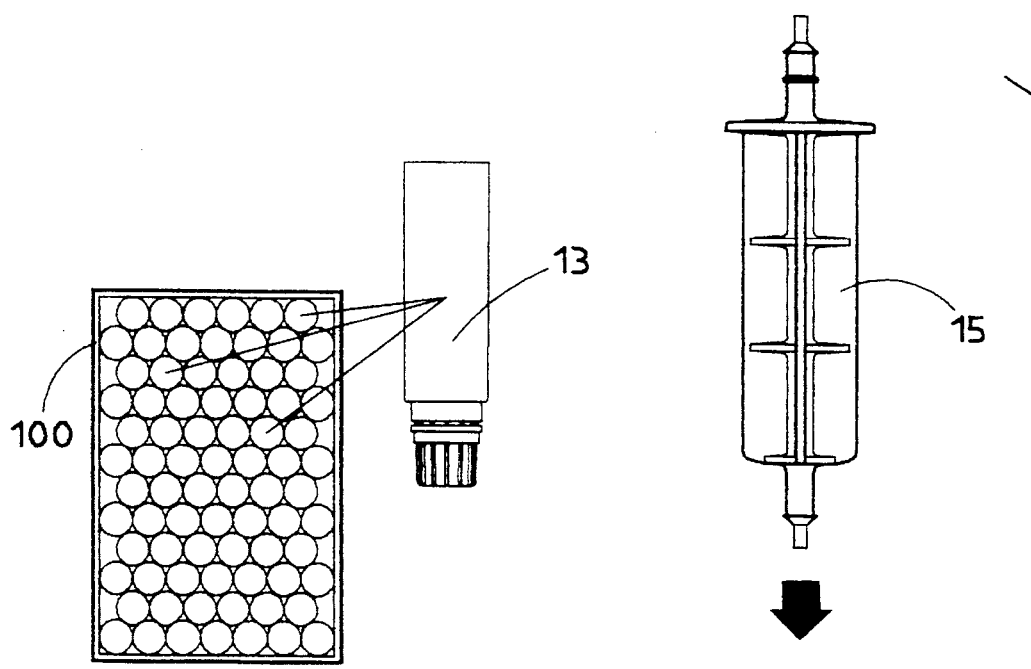
Fig.49
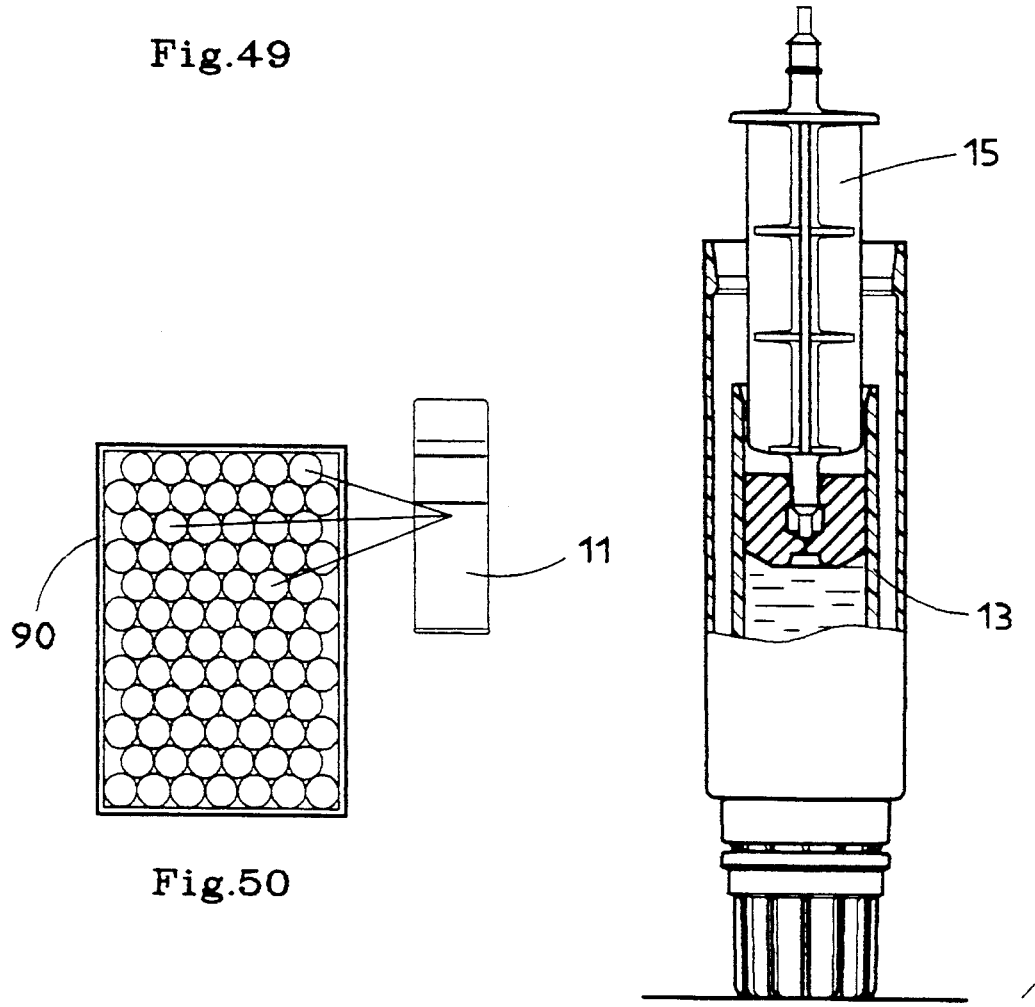
Fig.50
Fig.51

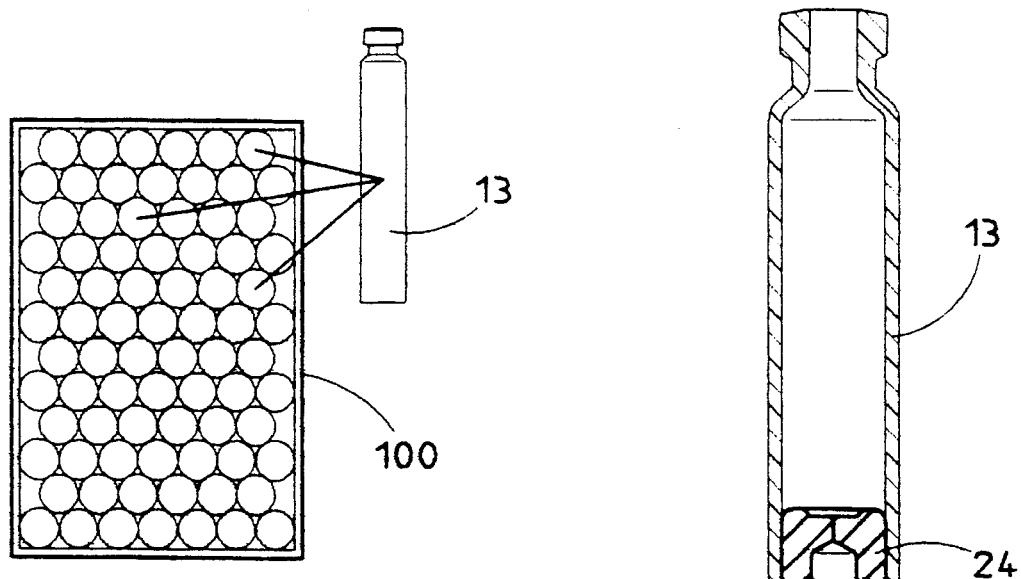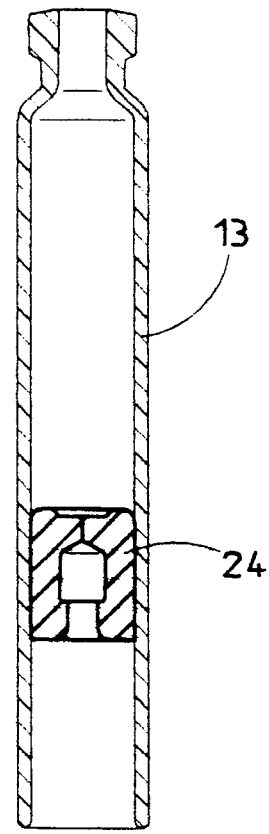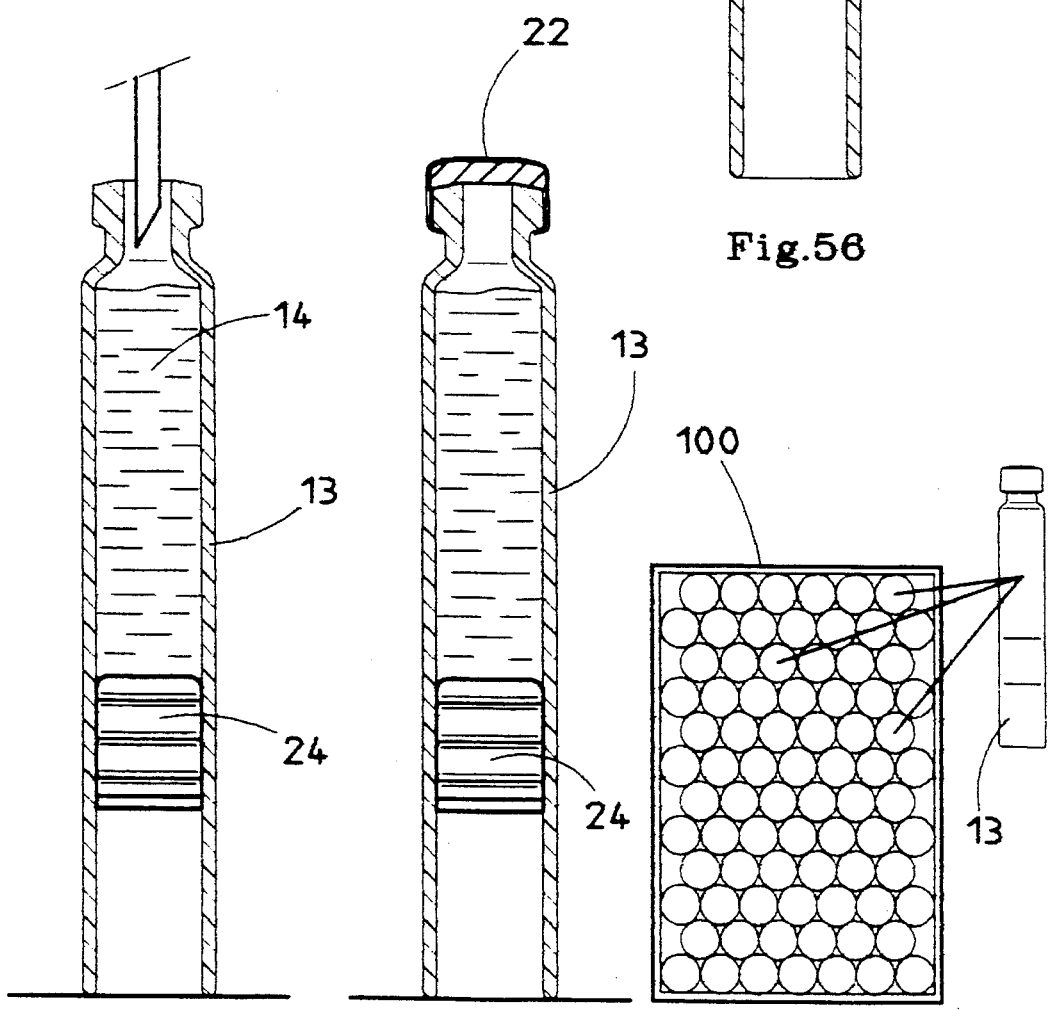
Fig.55  Fig.56
Fig.57  Fig.58  Fig.59

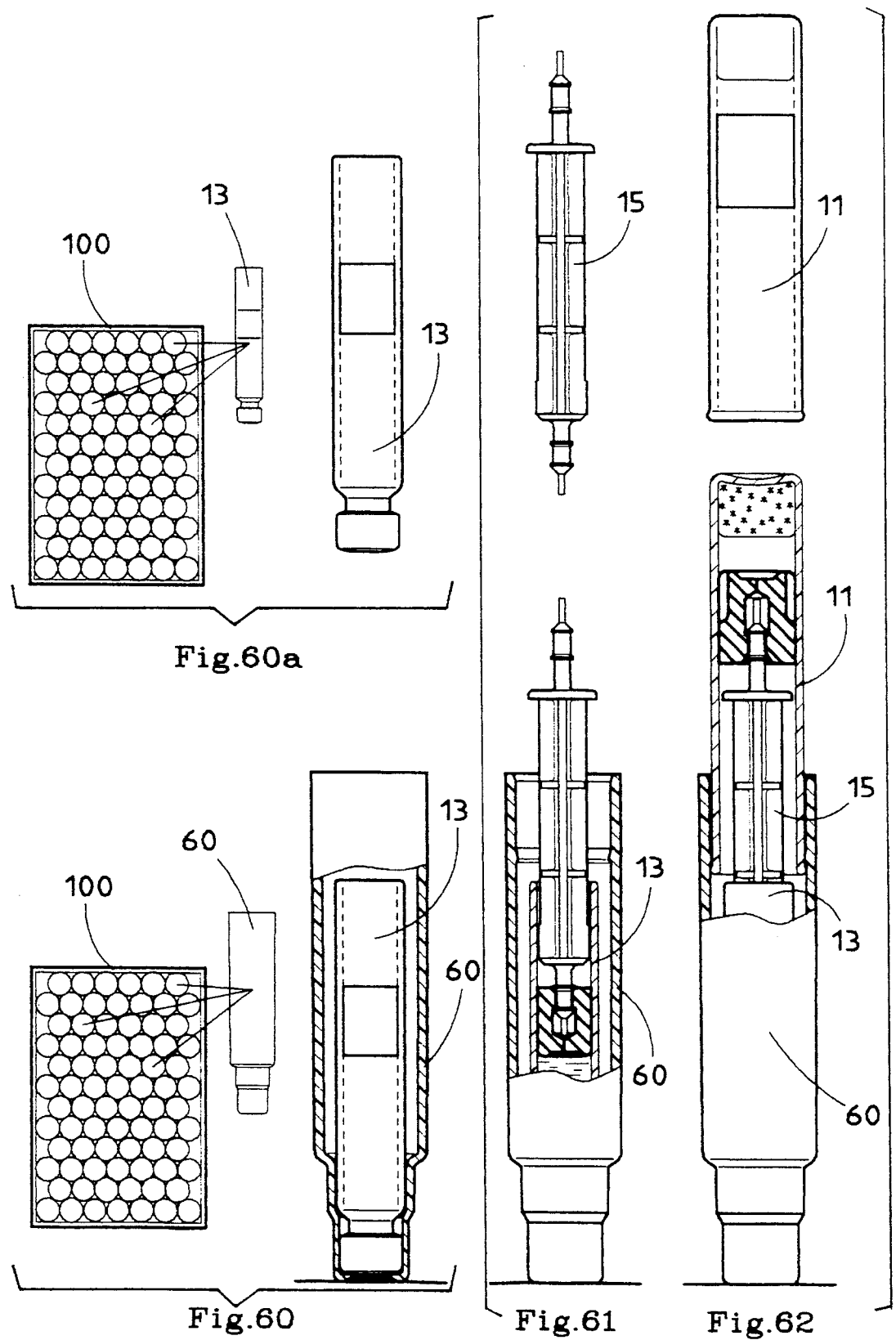

DEVICE FOR PREPARING A MEDICINAL SUBSTANCE SOLUTION, SUSPENSION OR EMULSION

The present invention relates to a device for the preparation of a solution, suspension or emulsion from a medicinally active substance with at least two components of which at least one is in liquid form.

The preparation before usage of a medication from one or several components stored in one hermetically closed assembly and intended to be mixed in this assembly without introducing external elements, poses multiple problems. A large number of bottles for two components have been developed for this purpose. Generally these hordes comprise one single container separated into two compartments by a movable closing member. Both these compartments are hermetically closed during storing. Before use of the medication in question, during the stage of putting the system to use allowance is made for mixing of the substances, of which at least one is in liquid form. For this purpose the movable closing member separating both compartments, is pushed in such a way as to penetrate into an enlarged zone or is provided with a bypass permitting the flow of liquid or solvent toward the other compartment which may either be liquid, solid or sticky, etc.

Manufacturing such double containers is not always easy and does not always fulfil the needs of the pharmaceutical industry for a particular application. A syringe with two components of the type mentioned above, is the subject of U.S. Pat. No. 4,014,330, which describes a syringe with two components respectively contained in two compartments closed by two stoppers or similar pistons. This device is constructed by using two members, which have to be assembled before use. The installation of the bottle, which defines the rear compartment, determines of necessity the use to which the system is put. The preparation and the leading together cannot take place in a closed environment so that important risks of contamination of the product by attending staff and the loss of sterility of the mixture occurs.

Furthermore, the active product is contained in a front container, open at both ends and furnished with screws. This poses problems notably from the time of conditioning a "lyophilisate", powder or liquid.

It is in effect imperative to prepare these active products in a cylindrical bottle with flat heat sealed bottom, to take care of the particular requirements of preparation of these substances by way of known equipment from the time of the empty preparation (washing, siliconizing, fixation with silicon film, "depyrogenization" and sterilization of the bottle), its filling (liquid, powder, "lyophilisate"), its closure (propping) and its conveyance towards an assembly unit with the component allowing for the compartment containing the dilutant.

The system as described in the U.S. Pat. No. 4,014,330 does not fulfil these requirements, for the active product should be prepared in the rear container and the preparation is in such conditions impossible by reason of its construction.

One of the problems posing itself in particular and which cannot so easily be resolved by systems where the components are contained in a single container with two compartments, is that of individual preparation of both components. In other words, the conditions of preparation and sterilization of the one component is not necessarily such as is expedient to the preparation of the other. One solvent cannot be treated in the same way as a lyophilisate or as certain powders. The lyophilisate does not resist the heat required to sterilize a solvent in an autoclave. The lyophilisate is separated from the solvent in a single container by a mobile and resilient stopper. The solvent is in permanent contact with such mobile stopper, so well so, that the partial steam pressure is constantly at its maximum. The risk of steam penetration along such mobile stopper is great and the duration of conservation of the lyophilisate may be compromised or time limited. Consequently the selection of resiliency is limited to that type where the capacity of barrier tightness is the most.

This last constraint imposes the establishment of proofs of evidence and compatibility, which is quite costly and long and handicaps pharmaceutical enterprises because they have to take a decision concerning preparation of their products in two chamber systems.

Added to these inconveniences is the increased risk of sterility of the container due to a humid environment. Besides, in conditions of monocompact preparation, a dry product is not sterilizable, has less a chance to grow germs if it is in a dry environment. This absence of risks disappears from the moment on where, in the same container, a liquid is prepared. The addition of conservation agents is undesirable and in certain cases even prohibited, notably for products with single use.

Products for multiple use in successive dosages are prepared with conservation agents, not to limit the growth of germs during storage, but in order to maintain the sterile status after preparation during the whole period of use, which may take several days.

Another problem cropping up and not easily solved by existing systems, is the control of supply from the time of preparation of the mixture without external action by a process of screwing, such as described in the European patent no. 0 298 067 B1.

The present invention proposes to mitigate these inconveniences by producing a device in which the risks of contamination from one of the components to the other are cancelled out, in which the basic components necessary for the preparation of a treatment mixture may be subjected to distinct operations with a view to their preparation and their conditioning, and in which the preparation is controlled in a tight and sterile environment without external action.

This aim is attained by the device of the invention as defined in claim 1.

In one advantageous embodiment the device has a sleeve in which is located the front container and at least partly the rear container.

This sleeve may be linked to a cup and to a dosage mechanism for the application of multiple dosages.

According to another embodiment the sleeve may be manufactured integrally moulding together with the front container.

Depending on the application for which the device is intended, the sleeve is equipped with a ferrule consisting of an opthalmic drop applicator or a nasal vaporizer, integrated into the front container.

In a preferred embodiment, the sleeve includes a first tubular element and a second tubular element, fitting into one another, the first tubular element containing the front container and the second secondary element containing the rear container.

Preferably the first tubular element allows has catches and the second tubular element has at least two tongue-like strips arranged to cooperate with the catches.

The stopper-piston-dishes of the device according to the invention each have a central groove and the conveyance shaft has means of tight and sterile coupling to the stopper-piston-dishes.

In an advantageous way the conveyance shaft allows for stop abutments arranged in order to give support to the surfaces with regard to the relevant stopper-piston-dishes, when the device is in a position of use.

When the device is in a charged position, the stopper-piston-dishes are adapted to ensure a tight and sterile closure of the relevant containers by supporting the inner walls of the containers in such a way that the containers may be charged and handled independently.

In all forms of construction the conveyance shaft is adapted to ensure a rigid, tight and sterile joining of the stopper-piston-dishes associated with the rear and front containers.

In the device according to the invention the front container is adapted to be able to receive different ferrules and applicators for performing therapeutical uses.

The present invention will be better understood with reference to the description of preferred examples of construction and the attached drawings, in which:

FIGS. 31 to 62 show schematically the different phases of preparation and assembly of the required components of the device according to the invention in different uses of the device and with different basic components relevant to these uses.

Figures 1, 2, 3, 4:
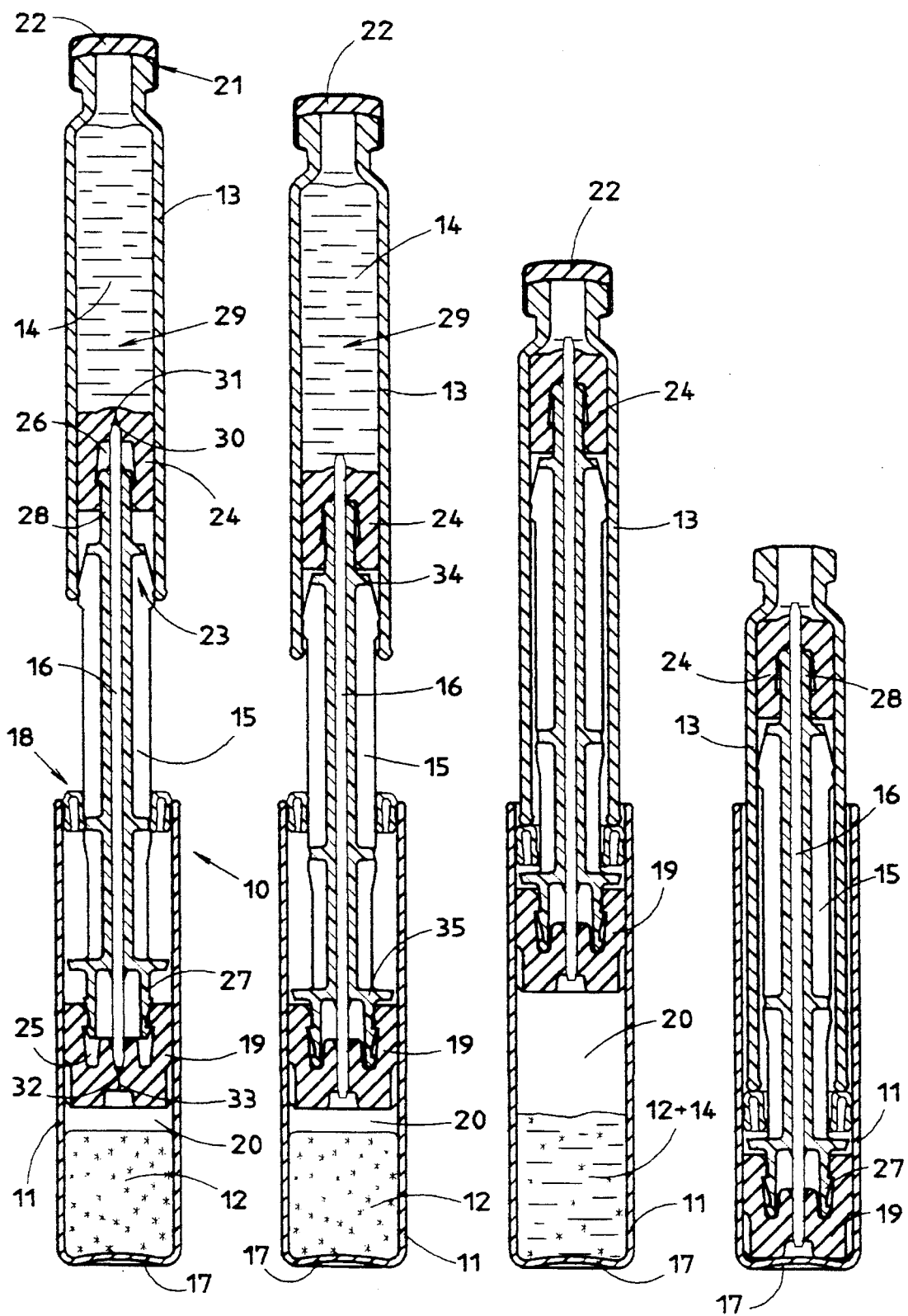
FIGS. 1 to 4 show one advantageous embodiment of construct, ion of the device according to the invention snowing successive phases of charging, putting to use and use.

FIGS. 1 to 4 show an advantageous form of construction of the device for the preparation of a medicinal solution, for example an injectionable solution, from two basic components. FIG. 1 in particular shows this device during a charging phase. It allows a first container 11, which contains lyophilisate 12, a second container 13, in this case containing a solvent 14, and a conveyance shaft 15 having a hollow conduit 16. The container 11, referred to as rear container, has a closed bottom 17 and an open end 18, and which there is fitted a stopper-piston dish 19, which defines inside the rear container a chamber 20 containing the lyophilisate 12. It must be noted that this lyophilisate 12 may be substituted by a different active substance such, as for example, a liquid, powder or a more or less pasty viscose substance. Container 13, here referred to as front container, is open at both ends. In the example given, the open end 21 is closed off by means of a capsule 22 mounted in fixed position. This capsule can be used with many bottles containing medicinal substances and may be made from a compound of plastics material to provide tightness, and from aluminium providing the mechanical strength and forming an antiseptic barrier. The open end 23 of the container 13 is closed off by a stopper-piston-dish 24. The stopper-piston-dishes 19 and 24 are respectively have a central groove 25, 26 in which respectively are arranged two ferrules 27 and 28 associated with the conveyance shaft 15. The stopper-piston-dish 24 defines chamber 29 containing the solvent 14, with the inner walls of container 13 and capsule 22. Depending on the medicinal substance contained in chamber 20 of the rear container 11, the solvent 14 may be substituted by a dilutant. Whatever the nature of the active substance of the rear container may be, the substance container in the front container is always in liquid form and is designed to be converted, together with the treatment substance, into a solution, suspension or emulsion derived initially from two basic components and is intended to be used in this connection within the framework of therapeutical treatment in injectionable form to be administered externally or internally by means of applicators, such as notably a needle, a trocar, a drop dispenser, a vaporizer, etc.

In the extension of its central groove 26 the stopper-piston-dish 24 receives a small attachment 30 in which is engaged the front end of the conveyance shaft. 15. In the extension of this attachment 30, the stopper-piston-dish has a pre-punched slit 31, which permits this member to play its role for closing relative to the stored liquid and to open during other phases, that is to say, during use and utilization. The resilient walls of stopper-piston-dish 24, which enclose the edges of the slit 31, are thick and this slit is arranged within a zone assuring increased compression of the edges of this slit when the stopper-piston-dish is in compression inside the front container in such a way that the closing off of the charged liquid is accomplished in an effective manner to guarantee simultaneously tightness and sterility of the chamber and the contents of the front container.

In a similar way the stopper-piston-dish 19 allows for a central recess 32, in which is engaged the other end of conveyance shaft 15. In its extension the stopper-piston-dish has a slit 33, which facilitates the function of the dish closed to the stored liquid and open during other working phases of the system, that is to say, when being put to use. There once again, the prepunched thickness of the material surrounding the lips of the slit 33, is sufficient when the stopper-piston-dish is installed in the rear container to assure a relatively important compression of the lips to guarantee simultaneously tightness and sterility of the chamber 20 of the rear container 11.

In the form of construction shown, the interior diameter of the rear container is substantially equal to the exterior diameter of the front container so that they could be fitted at least partially into one another during use. For obvious reasons of simplicity for manufacture and production, both containers have a generally elongated cylindrical shape in section. Due to the dimensions of both containers, the stopper-piston-dish 19 has a diameter, which is greater than that of the stopper-piston-dish 24, at the moment of putting to use, which is represented in FIG. 2, initiated by pressure exerted on the axis, preferably at the bottom 17 of the rear container, the front container being kept in position, the ends of the conveyance shaft respectively fitting into slits 31 and 33 of stopper-piston-dishes 24 and 19, which results in putting the chambers 20 and 19 into communication and allowing the flow of solvent 14 along the conduit 16 into the chamber 20 containing the lyophilisate 12. The diameter and the length of the conduit 16 are dimensioned in such a way that one obtains a controlled supply from the time of flow of solvent 14 along this conduit 16. It will be noted that in the transition the ends of the conveyance shaft are not formed by bevellings, whose function does not consist of piercing a membrane, but by a level section disposed perpendicularly along the axis of the conveyance shaft and possibly prolonged by a weak cut up zone.

This geometry permits an easy introduction into the tight and sterile slits, the ends being intended to separate the lips of those slits to open the dish of the stopper-piston-dish contrary to numerous well-known systems where a conveyance presents a bevelled end, the function of which is to perforate a membrane. The tightness between the membrane and the bevelled end cannot be ensured if the thickness of the membrane is distinctly more than the length of the bevel, which is incompatible with a compact construction and with the facility to penetrate this membrane. Besides, it will likewise be noted that the conveyance shaft 15 is equipped with a first disc 34 and a second disc 35 which, except for storage of liquid, are respectively in support of the surfaces in regard to stopper-piston-dishes 24 and 19. These discs have as function to define precisely the degree of penetration of the ends of the conveyance shaft into the relevant rear and front containers.

When the user continues to press on the bottom 17, all solvent contained in the front container 13 flows into the chamber 20, enters into contact with the lyophilisate 12 to form a solution 12 plus 14, which constitutes the medicinal substance in question. By way of pressure and differences of the surfaces between both the stopper-piston-dishes, the stopper-piston-dish 24 lodges itself to the front end of the front container 13 and the stopper-piston-dish 19 gets into a position that it becomes possible to ensure the de-aeration, the bottle having been equipped with de-aeration suitable to function regarding medicinal solution. If this solution is intended for injections, the ferrule will be a needle. If this solution is meant to be transferred to a transfusion bag, the ferrule will be a trocar. If the solution is meant for a different use, the ferrule will be chosen accordingly. Whatever the ferrule will be, the solution is transferred along the conduit 16.

To this effect the bottom gives support to the rear container 11 fitted on front container 13. The stopper-piston-dish 19 progressively sinks inside the rear container 11 until such moment when it touches the bottom 17. To prevent a re-utilization of the device, particularly in the case of it being used as a syringe, the means of joining the ferrules 27 and 29 with the conveyance shaft 15 respectively with stopper-piston-dishes 19 and 27, are sufficiently weak so that, the stopper-piston-dishes separate at that moment when use would attempt to withdraw the front container from the rear container, the re-charging of a liquid into the inside of the device is rendered impossible.

Figure 5:
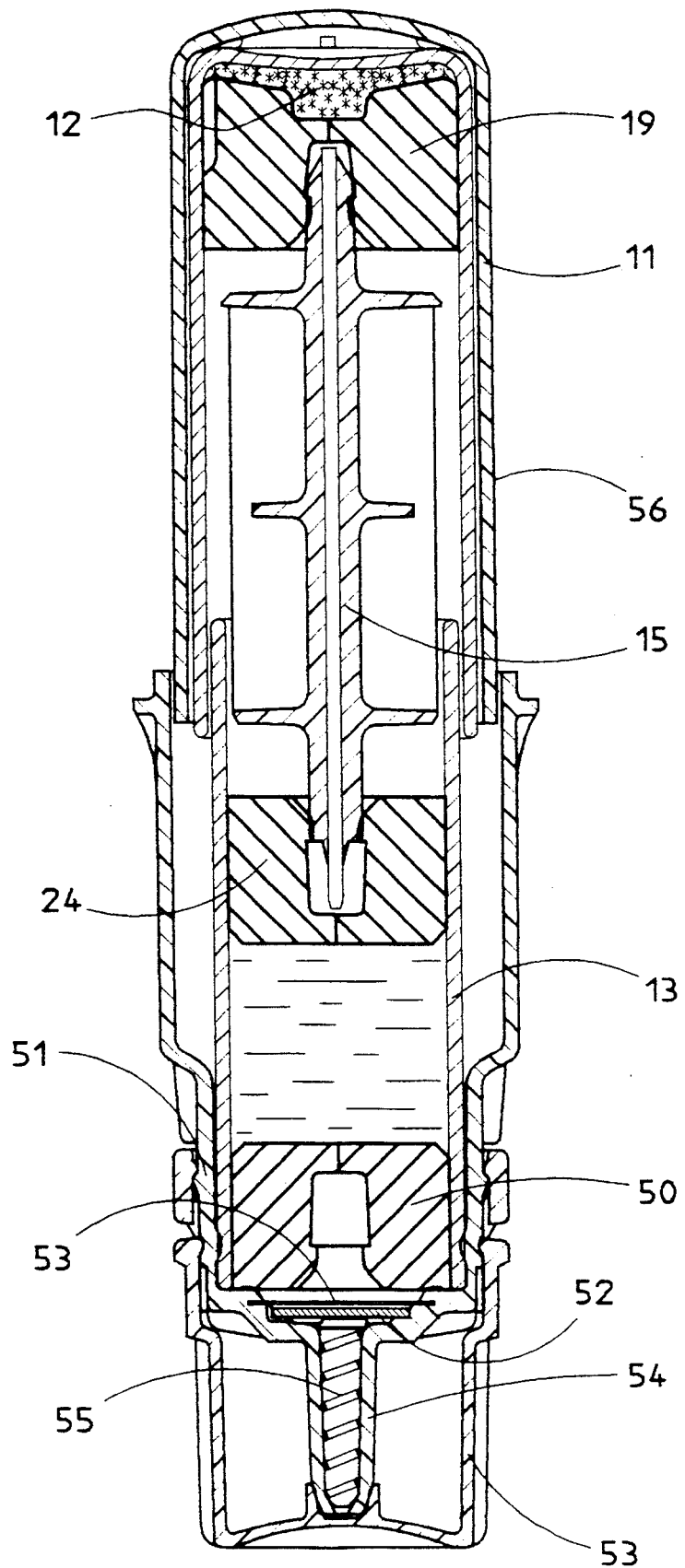
FIG. 5 show one particular embodiment of construction of the device intended for use as ophthalmic drops dispenser.

FIG. 5 shows the device according to the invention adapted with, a view to an application in opthalmic treatments. In such a case both the containers, the rear and the front, 11 and 13, are prefitted. The rear container 11, which contains a lyophilisate 12, is completely void of air. The stopper-piston-dish 19 being engaged inside the container, is compressed against the material, which it contains. The advantage of this construction is such, that it permits to suppress purging or bubbling and avoids an oxydation of the mixture after its preparation, that is to say, at the moment of putting the device to use.

The front container 13 which, as will be remembered, is open at both its ends, is closed at one of its ends by stopper-piston-dish 24 and at its other end by plug 50. A capsule 51 caps this plug and a filter 52, such as a silver patch having an oligodynamic function, is inserted between this capsule and the plug. The silver patch may be substituted by a different material, such as for instance silver oxide or a compound containing substances with similar properties, A protection hood 53 closes this assembly. A ferrule 54 at the injection tube spiral 55 fits at the end of capsule 51. In this case the conveyance shaft 15 is advantageously constituted by in synthetic material integrally moulded in one piece. It will be noted that the plug 50 has a geometry which is sensibly identical to that of stopper-piston-dish 24 and that it functions according to the same principles, at least regarding its central opening which makes of it a dish consisting of a prepunched slit meant to be open at the end of the conveyance shaft during utilization of the device.

Likewise in this construction the capsule 51 has a skirt sufficiently long to conceal a part of the rear container 11 near its open end. This rear container itself is located inside a hood 56 of moulded synthetic plastics material ensuring its protection. The hood 56 is prefitted into the skirt of the capsule 51. For other uses, the hood 56 could be left out and the rear container could be directly engaged around its upper open part, inside the skirt of capsule 51.

Figure 6:
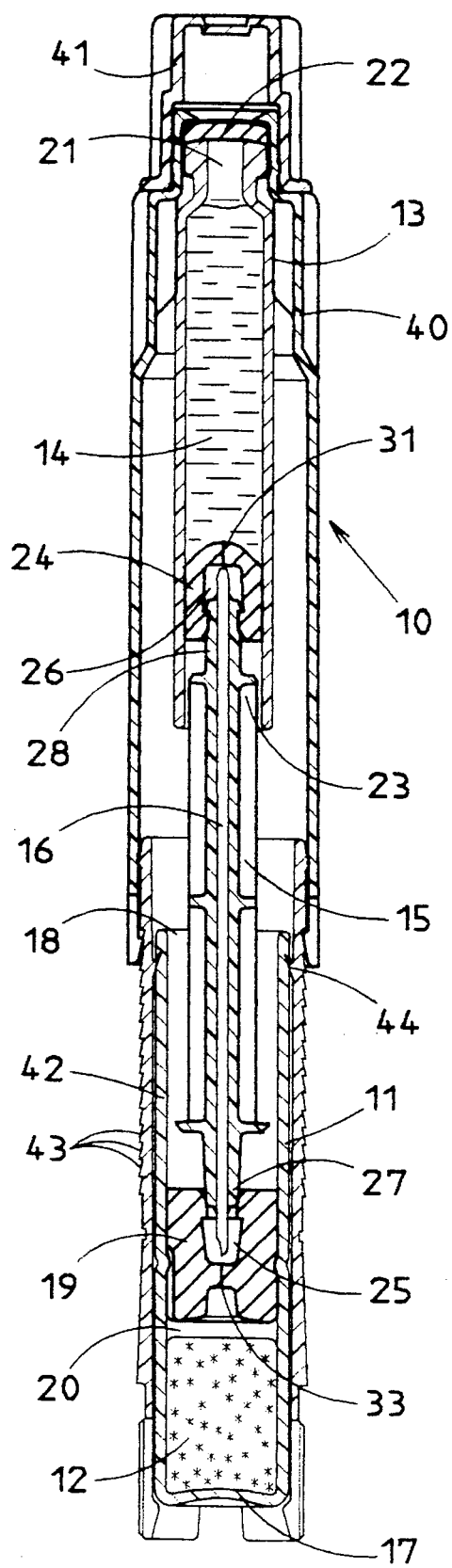
FIGS. 6 to 9 show a different embodiment of construction of the device according to the invention showing successive phases of charging, putting to use, at the beginning and on completion of use.
Figure 7:
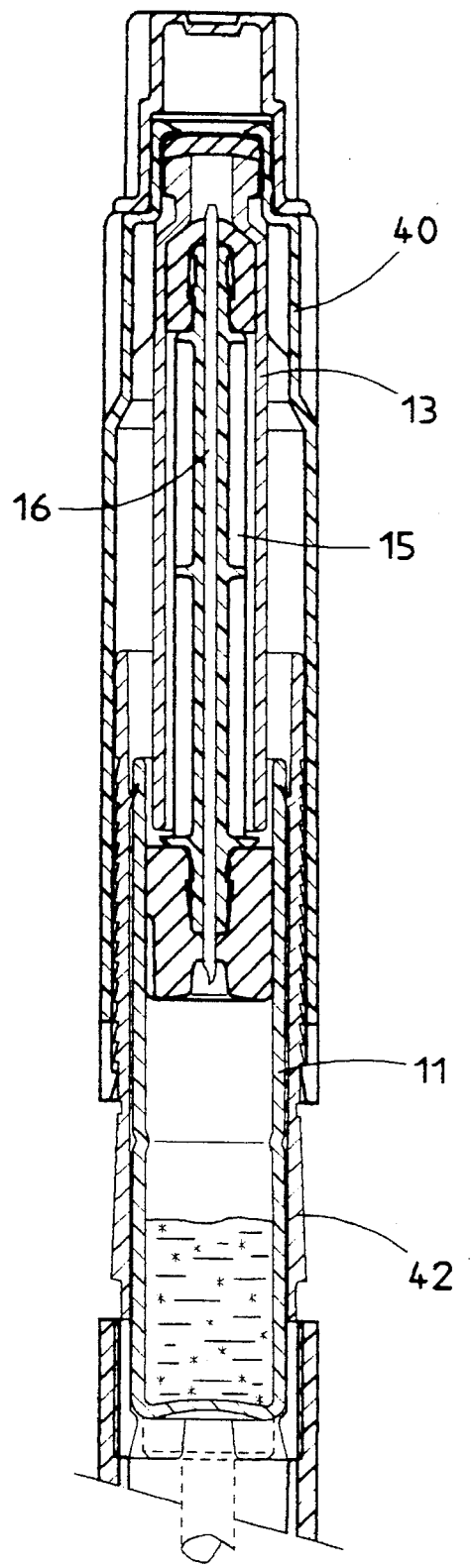

FIGS. 6 to 9 illustrate another form of construction of the device meant to be used as a syringe for the injection of a medicinal substance in question. FIG. 6 shows the liquid when stored. FIG. 7 during use, FIGS. 8 and 9 the use within the framework of a mechanical system of multi-dosages. As before, the device has a rear container 11, containing for example a lyophilisate 12 and a front container 13 containing for example a solvent 14, so that there is a conveyance shaft 15 meant to permit communication between both these containers along a tubular conduit 16. The rear container 11 has a bottom 17 and has an opening 18 at its end opposite to the bottom 17. It is closed by stopper-piston-dish 19, which defines a chamber 20 containing the lyophilisate 12. The front container 13 has an upper opening 21 closed by an inserted capsule 22. As this container is open at both its ends, its other end 23 is closed by stopper-piston-dish 24. Stopper-piston-dish 19 has a central groove 25 and stopper-piston-dish has a central groove 26, both these stoppers being meant to respectively receive two end ferrules 27 and 28 at the ends of the conveyance shaft 15. The stopper-piston-dish 24 has a prepunched slit 31 serving as a dish which is intended to receive the end of the conveyance shaft 15 and likewise the stopper-piston-dish 19 has a prepunched slit 33 serving as close, which is meant to $dish the other end of conveyance shaft 15.

Several parts are identical to those described with reference to FIGS. 1 to 4. The front container 13 is located inside a first tubular element 40, whose front end is capped by a protection hood 41 and the rear container 11 is located inside the second tubular element 42, partly engaged inside the first tubular element 40. In the storage position represented by FIG. 6 both tubular elements 40 and 42 define a cavity, preferably cylindrical, inside which is located the device 10 represented by FIG. 1. With a view to putting this device to use, the second element 42 has a series of catches 43, which may be distributed along the whole periphery of the element or singly above a free zone of this periphery. These taps are intended for cooperating with at least one flexible tongue-strip 44 arranged inside the lateral side of element 40, with a view to generate predetermined braking forces for regulating the axial displacement of both elements 40 and 42 and to define anti-return abutments preventing the recoiling or the withdrawal of the second element 42, when it is engaged inside the first element 40.

FIG. 7 shows the phase of putting to use and the preparation of the mixture of two components. In this phase the tubular element 42 has been sunk in the tubular element 40 in order to effect the displacing of the rear container in the direction of the front container. It results in a part penetration of both ends of the conveyance shaft into the slits constituting the relevant dishes of stopper-piston-dishes, the displacing of stopper-piston-dish 24 axially in the front container and the flow of solvent into the chamber 20 where there is lyophilisate 12. Finally in this phase of use, the mixture of both substances or basic constituents of the medicinal substance is determined and this substance Is ready for use.

Figure 8:
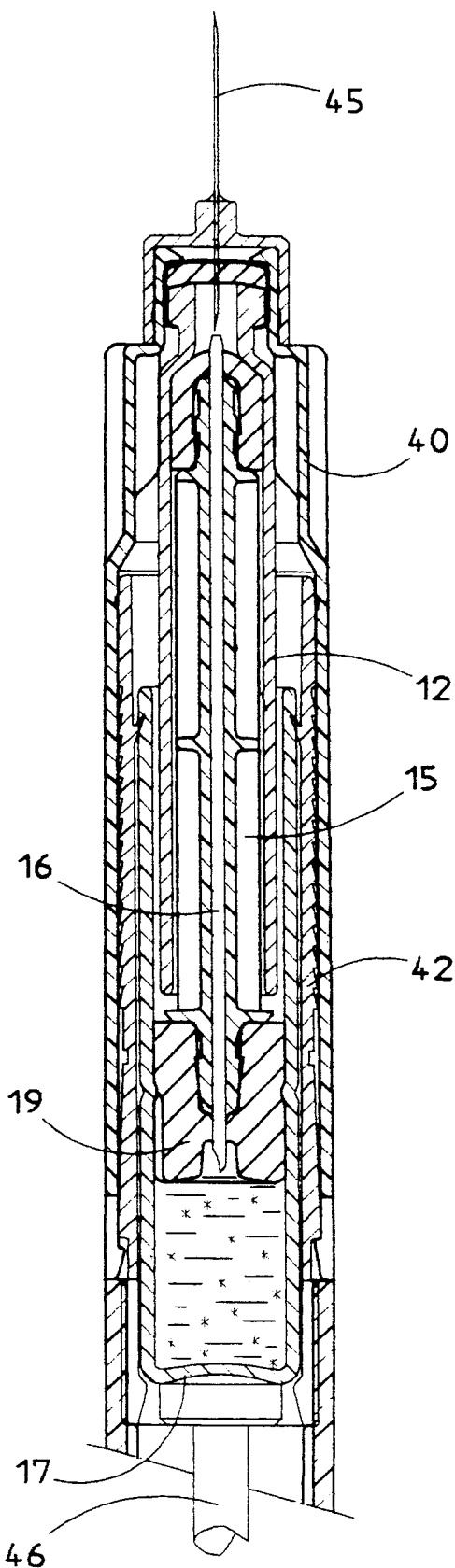

FIG. 8 illustrates the final phase of preparation, which consists of de-aeration or de-bubbling the device, which in this case is equipped with a needle 45 to inject the medicinal substance in question. The second tubular element 42 has been completely returned inside the first tubular element 40, the rear container into which is filled the solution of lyophilisate that has been completely de-aerated, and pushing is exerted on the bottom 12 of the rear container by means of a suitable button 45 permits the stopper-piston-dish to support the solution contained in the rear container. In this connection this stopper-piston-dish has the function to compress the solution along the conduit 16 of conveyance shaft 15 in the direction of the injection needle 45.

Figure 9:
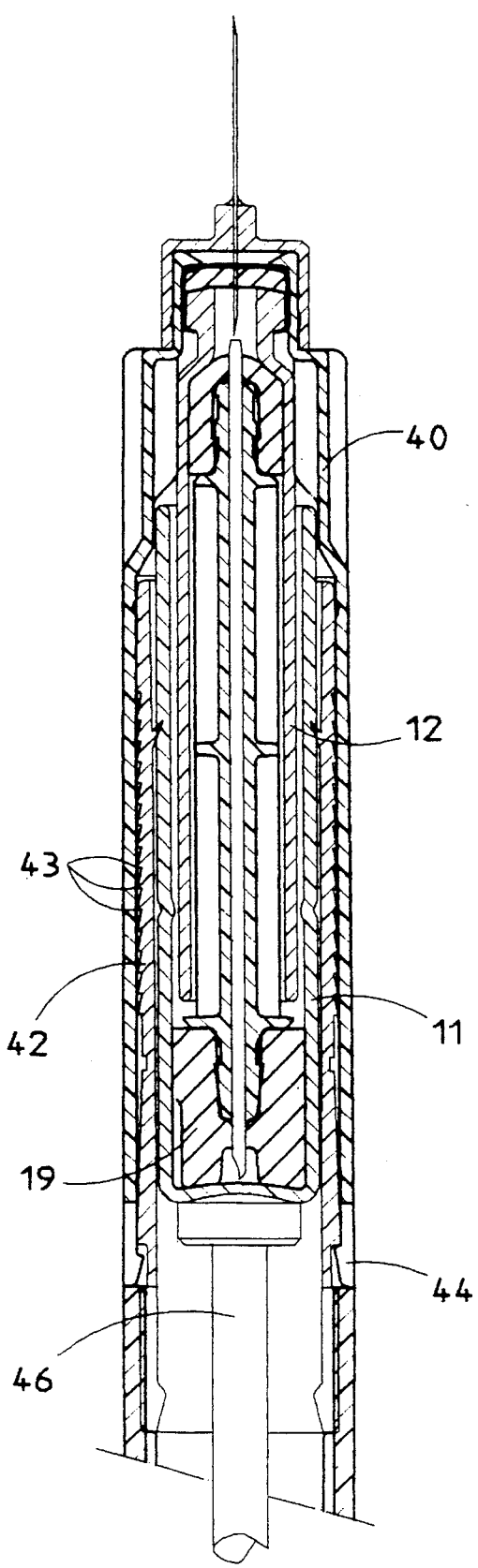

At the end of the phase of use illustrated in FIG. 9, the button 46 has pushed back the rear container in the direction of the front end of the device in such a manner that the stopper-piston-dish 19 has been compressed completely inside the rear container and that almost all of the injectionable substance in question has been evacuated. Besides, it will be noted that the second cylindrical element 42 and the catches 43 cooperate with the flexible tongue-like strip 44 to block both elements by interaction with one another and prevent the return of the second elements into its initial position. These members ensure that the device is guaranteed not to be re-used.

Figure 10:
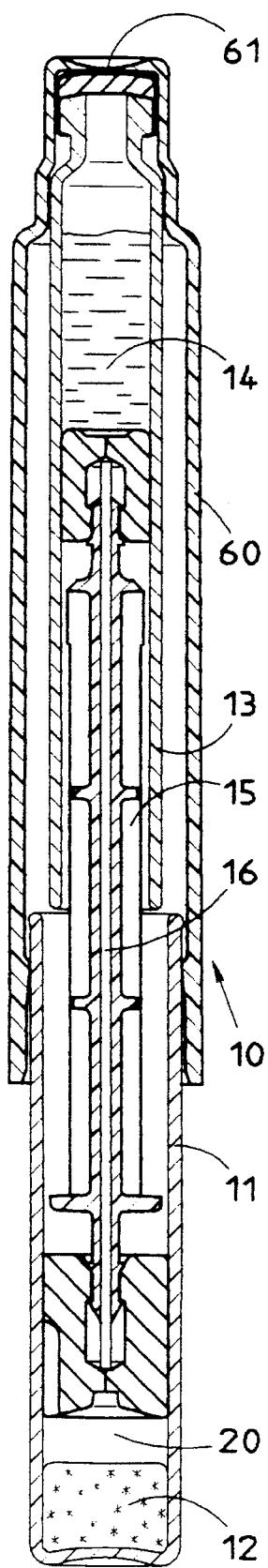
FIGS. 10 to 13 show a variant constituting an improvement of the device such as shown in FIGS. 1 to 4.

FIGS. 10 to 13 show a variation which may be considered as an improvement of the device as is represented by FIGS. 1 to 4 and in fact corresponding to that which one could call the primary reservoir—the device such as represented by FIG. 10 of a charged stage corresponds substantially to the combination of the primary reservoir, such as represented by FIG. 1, with its rear container 11, its front container 13 and its conveyance shaft 15, located at least partially at any rate inside a cylindrical body or sleeve 60. This sleeve is preferably made of moulded synthetic material.

Figure 11:
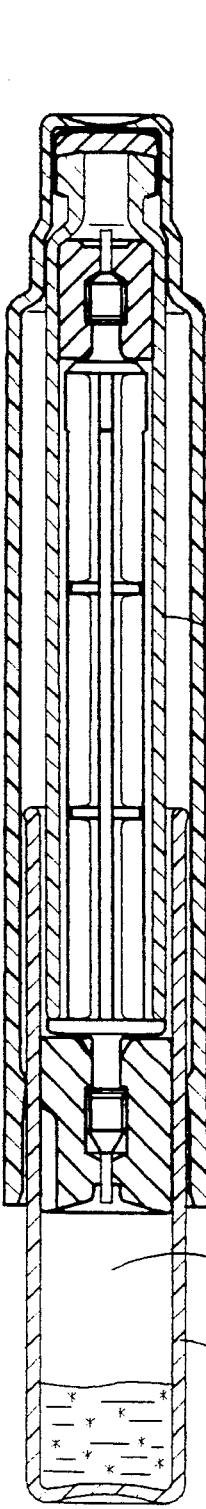
Figure 12:
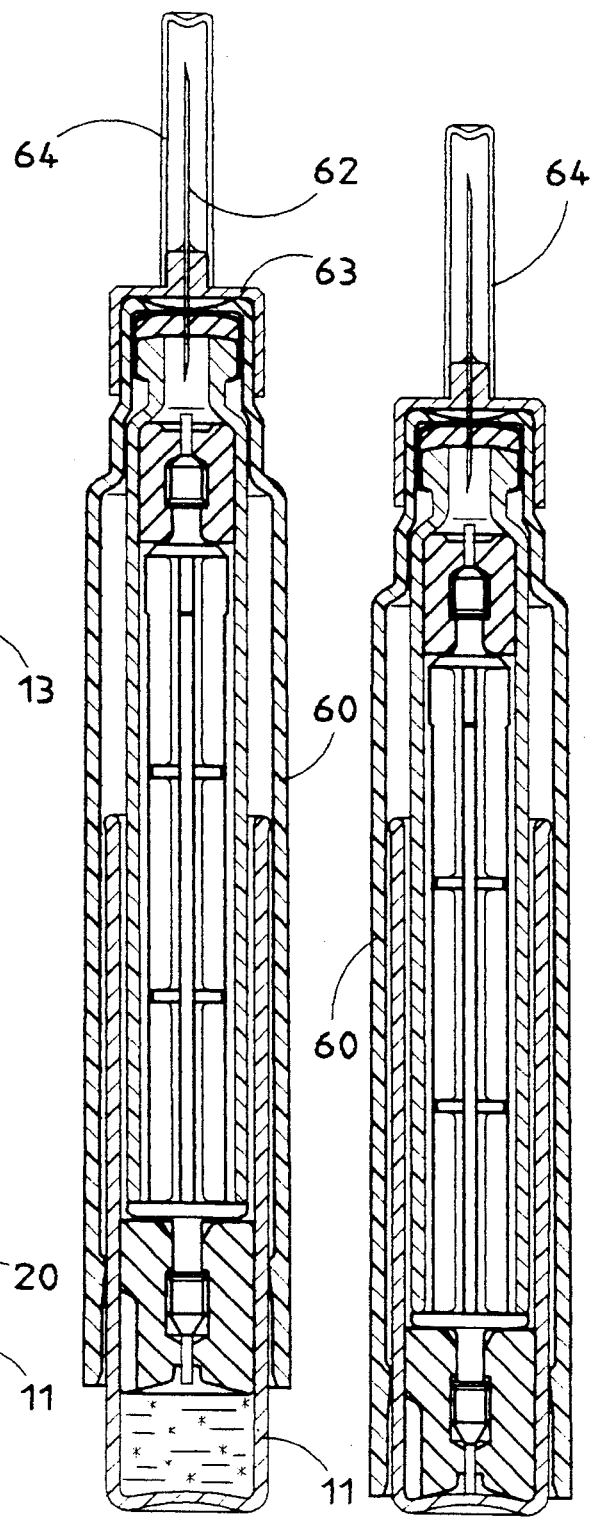

Its frontal end has a zone of lesser thickness 61 being easily perforated by a suitable needle, as is shown in FIG. 12. Besides, it will be noted that the conveyance shaft contains the internal conduit 16, which preferably is constituted by a hollow injection tube of metal, which is overmoulded, FIG. 11 shows the device 10 when put to use, solvent 14 having been transferred along the conveyance shaft 15 into a chamber 20 of the rear container 11 for dissolving the lyophilisate.

FIG. 12 illustrates the phase of de-aeration of the syringe, obtained by adjunction of a premounted needle 62 onto a flange 63 and protected by a protection hood 64. It will be noted that the rear container 11 has been moved in the direction of the front end of the device in order to evacuate the air contained in the chamber 20 of the rear reservoir after preparing the mixture.

Figure 13:
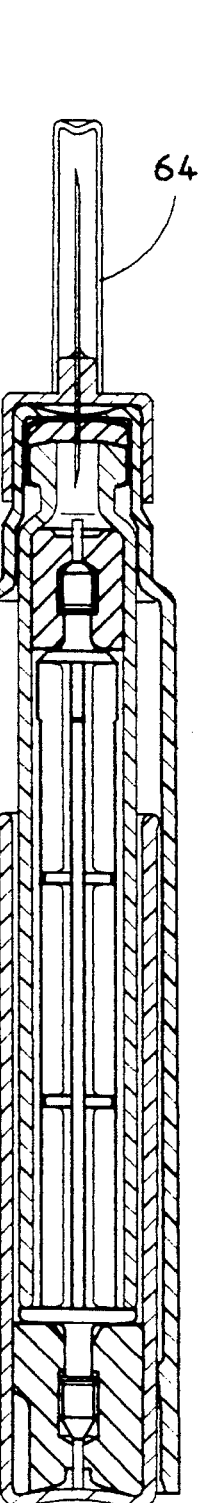

FIG. 13 shows the device after use. It will be noted that the hood 64 has been repositioned at the end of the device to mask the needle and to prevent that the caring staff is accidentally wounded by such pointed implement. Both containers, rear and front, are encased into one another and located completely in the sleeve 60, which prevents the re-use of the syringe, making it impossible, without breaking the sleeve, to pull the rear container backwards. Even if this operation could be accomplished, the safety obtained due to an effective separation of stopper-piston-dishes and the conveyance shaft remains as has been explained with reference to the description of FIGS. 1 to 4.

FIGS. 14 to 18 illustrate a different form of construction based from the preceding construction in which the sleeve 60 has been replaced by a sleeve 60 longer than sleeve 60. To this sleeve 60 is adjoined a cup 70 as well as a dosage mechanism 71, commercially known under the name "PEN" or the like.

Figure 14:
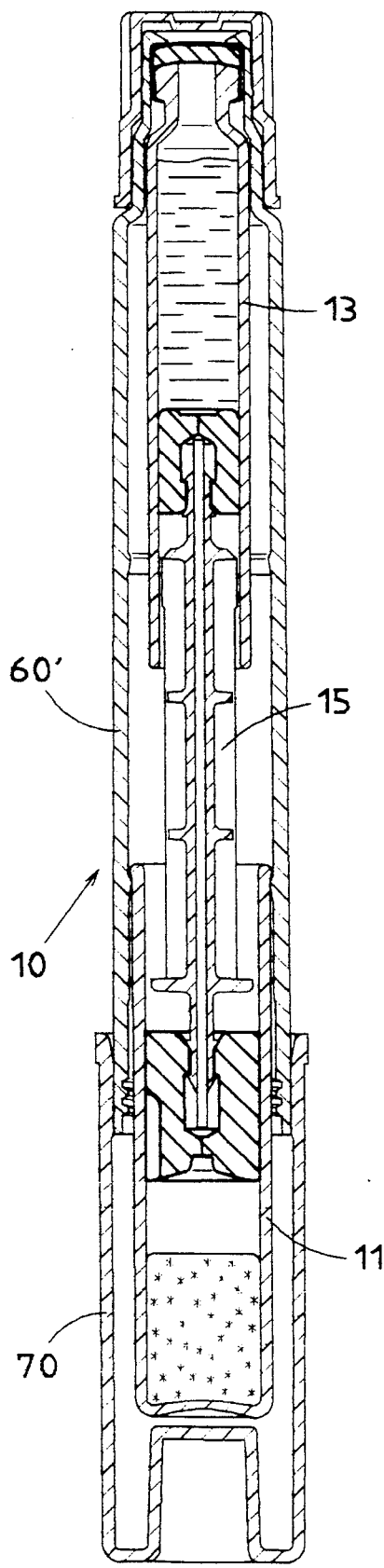
FIGS. 14 to 18 show another form of construction of the device used as a syringe connected to a dosage mechanism for the application of multiple dosages.
Figure 15:
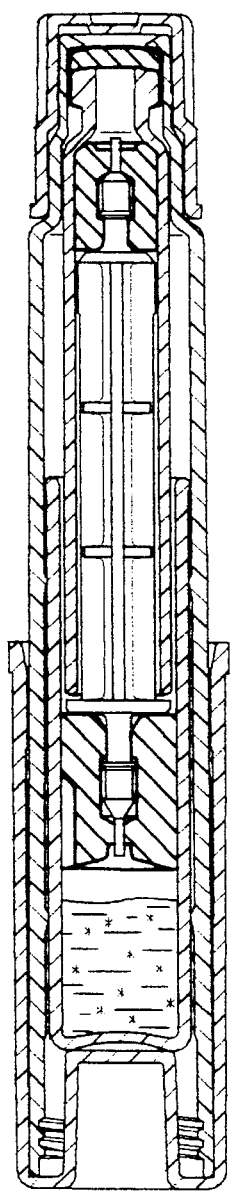
Figure 16:
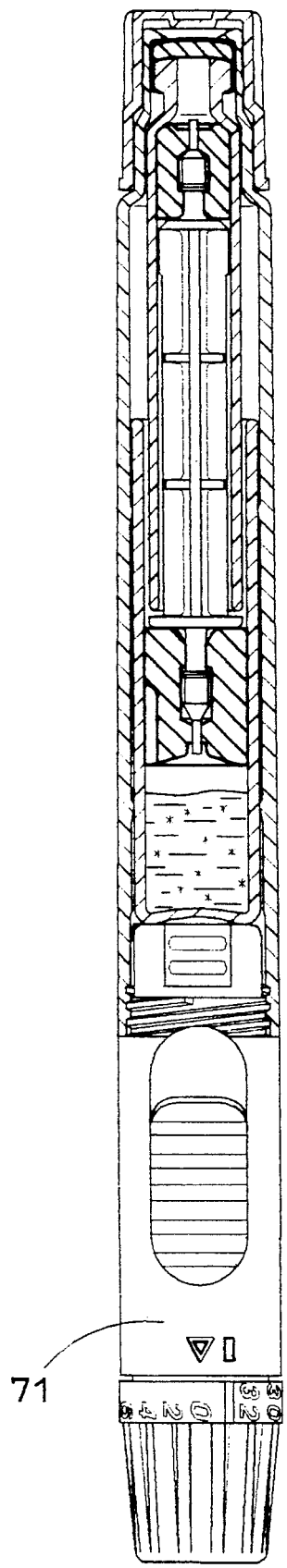
Figure 17:
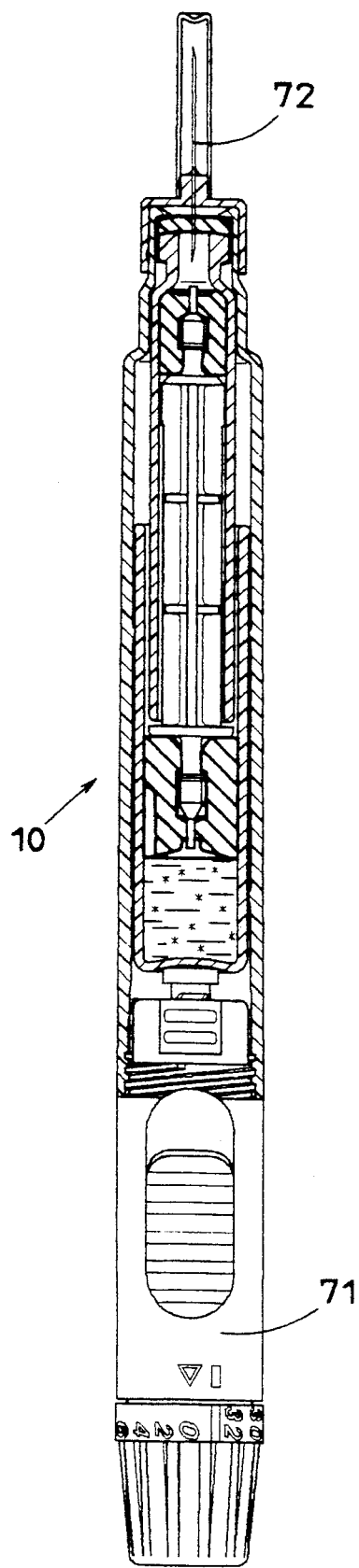
Figure 18:
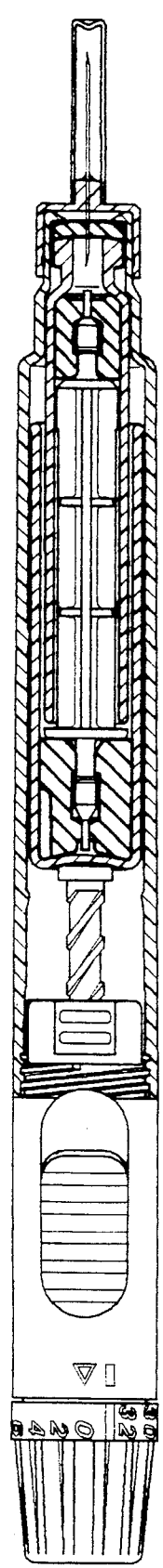

As previously, the device 10 has the following main elements, being the rear container 11, the front container 13 and the conveyance shaft 15. This is depicted by FIG. 14 in a state of charging, FIG. 15 represents the activated device, equipped with a dosage mechanism 71, FIG. 17 shows the activated device equipped with a dosage mechanism and provided with an injection syringe 72. FIG. 18 shows the device after use.

Figure 19:
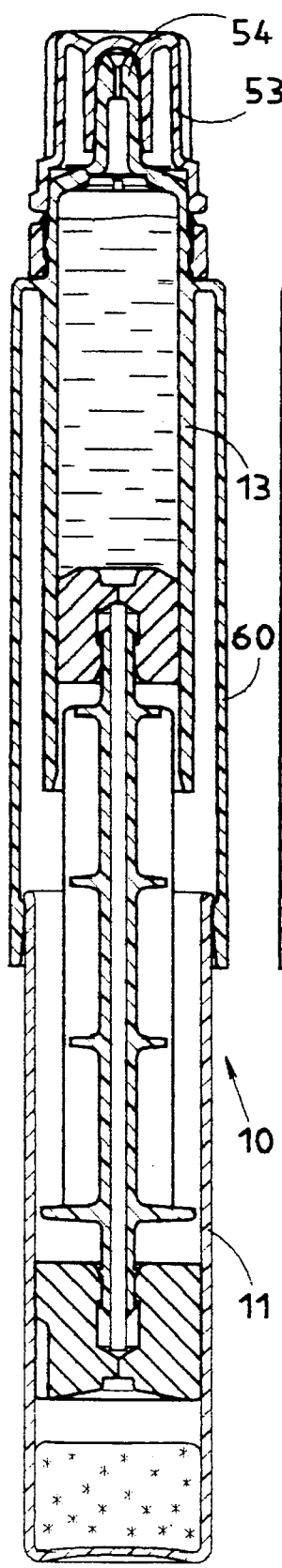
FIGS. 19 to 22 show the device according to the invention, adapted for opthalmic field use.
Figure 20:
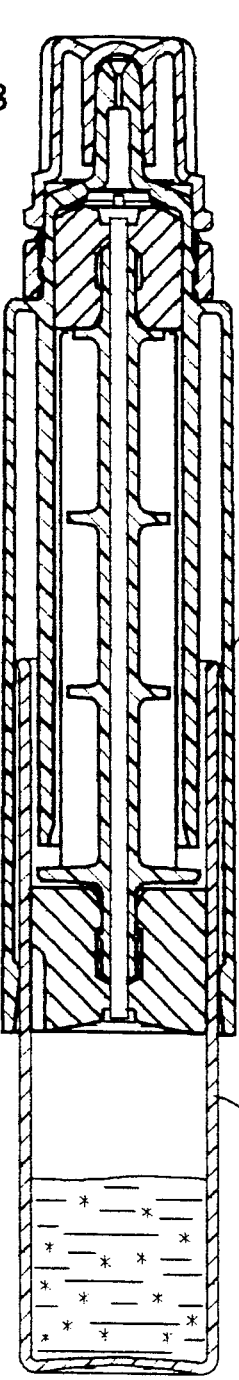
Figure 21:
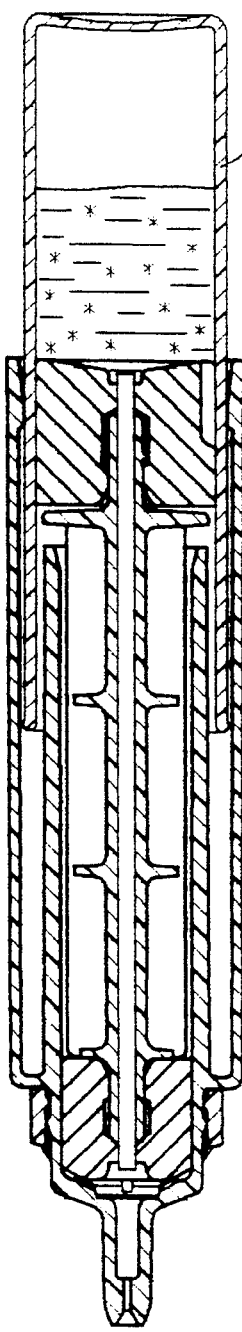
Figure 22:
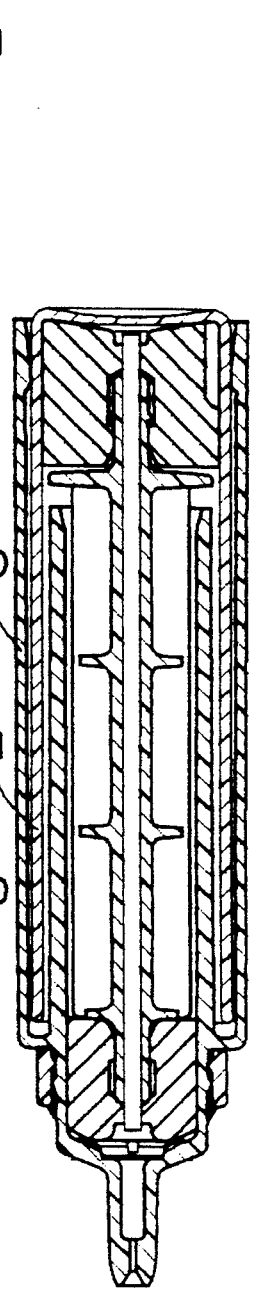

FIGS. 19 and 20 illustrate the device adapted with a view to application in the ophtalmic field. It will be noted that in this construction the front container 13 is moulded from synthetic material integrally with the sleeve 60, which contains the front container and partially, at least when charged, the rear container 11. The sleeve 60 is extended by an ophtalmic drops applicator constituted by a ferrule 54 substantially identical at least in its function to that described with reference to FIG. 5. This ferrule could likewise be in the form of a nasal vaporizer. A protection cap 53 ensures a tight and sterile closure of the device during the phase of charging shown by FIG. 19, and the phase of use is shown by FIG. 20. The phase of use is shown by FIG. 21. The completion of use is shown by FIG. 22. It will be noted that the rear container 11 is integrally made inside the sleeve 60, which prevents the re-use of the device.

Figure 23:
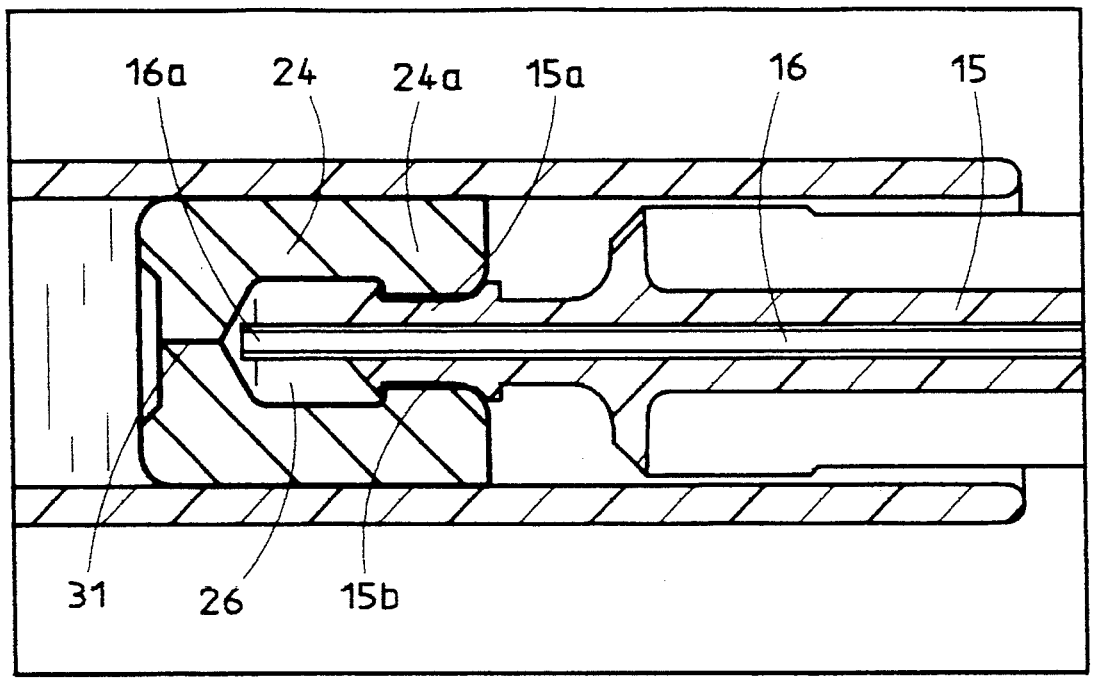
FIGS. 23 and 24 show enlarged views of stopper-piston-dishes in a position of rest.

FIG. 23 shows an enlarged view of the stopper-piston-dish 24 and the relevant end of the conveyance shaft equipped with its central conduit in charged position. In this position the end 15a of the conveyance shaft is exactly engaged in a first zone 24a of the stopper-piston-dish 24, this engagement being accomplished in such a manner as to guarantee perfect tightness and a sterile barrier thanks to an elastic compression being exerted at the level of surface 15b. In this position the end 16a of the conduit 16, which is likewise open by a level section substantially perpendicular to the axis of the conduit, is in support of the entrance of the slit 31, which constitutes the dish of the stopper-piston-dish 24.

As mentioned before, this dish is kept tightly closed by the compression of the relatively important material surrounding its lips. The opening of this dish is not accomplished, as in numerous previous systems, due to pressure exerted by a liquid substance, which is forced along the conduit 16, but well under mechanic pressure by the introduction of the end 16a of this conduit. Due to this fact the tightness between the walls of the conduit 16 and the lips of slit 31 remains preserved and the central groove 26 of the stopper-piston-dish 24 does not enter into contact with any component of both the containers nor the substance in question.

Figure 24:
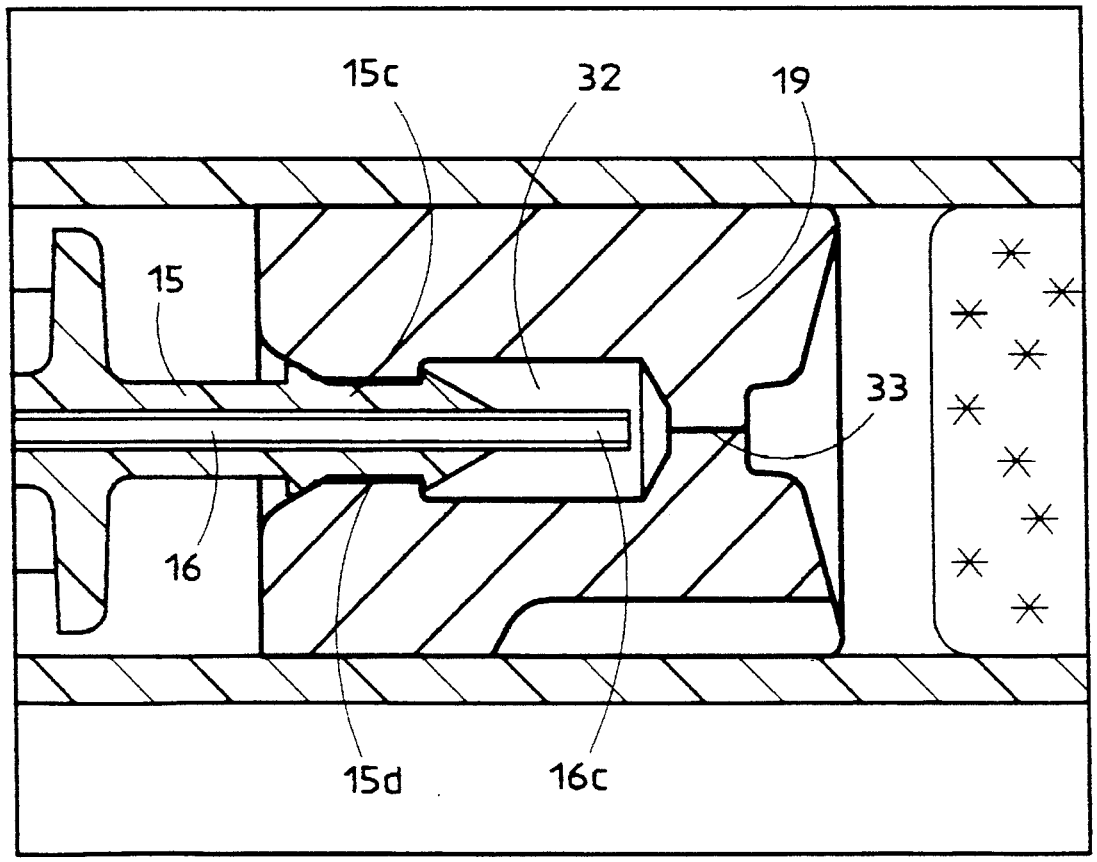

FIG. 24 shows an enlarged view similar to that of FIG. 23, but concerning the stopper-piston-dish 19 during a state of charging. As previously, the other end 15c of the conveyance shaft 15 is engaged in a central groove 32 of the stopper-piston-dish 19 and the end of 16c of the conduit is a support to the entrance of slit 33 serving as dish. Tightness and sterility are guaranteed on the level of surface 15d due to the pressure exerted by the material of the stopper-piston-dish 19 on the end 15c of the conveyance shaft in the zone concerned. The same tightness is ensured between the end 16c of conduit 16 and the lips of slit 33 when this end is engaged in the slit.

It will be noted, besides, that for both the stopper-piston-dishes 19 and 14, respectively shown by FIGS. 24 and 23, the ends 15A of one part and 15c of a different part of the conveyance shaft 15 present a form of harpoon provided with stop abutments guaranteeing a relatively firm connection between the conveyance shaft and the stopper-piston-dishes during the phase of charging. Due to this form of harpoon these ends 15a and 15c define stop abutments and the means of liaison, which permit defining an extremely precise positioning of the stopper-piston-dishes inside the device.

Figure 25:
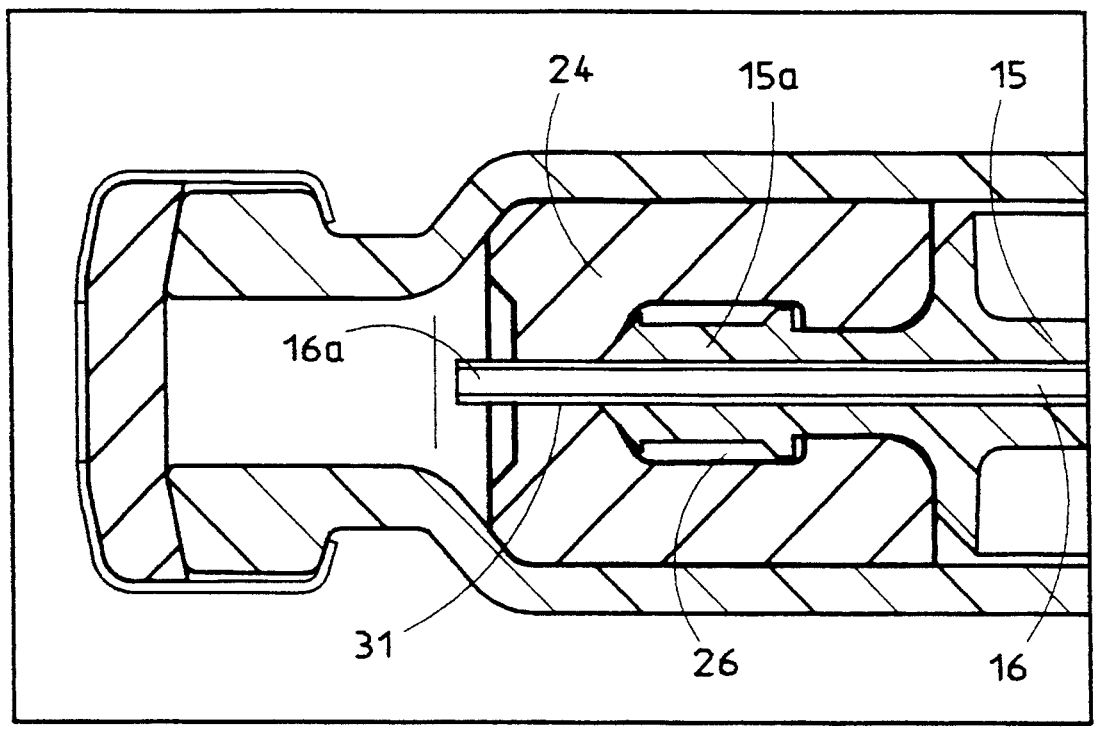
FIGS. 25 and 26 show enlarged views of stopper-piston-dishes in a position of putting to use and of use.

FIG. 25 shows a stopper-piston-dish 24 of FIG. 23 in the position of putting the device to use. The end 15a of the conveyance shaft has been pushed back inside the contral groove 26 and the end 16a of the conduit 16 has been pushed back along the prepunched slit 31. This figure shows clearly, that these zones of tightness and sterility previously mentioned are presented in this phase.

Figure 26:
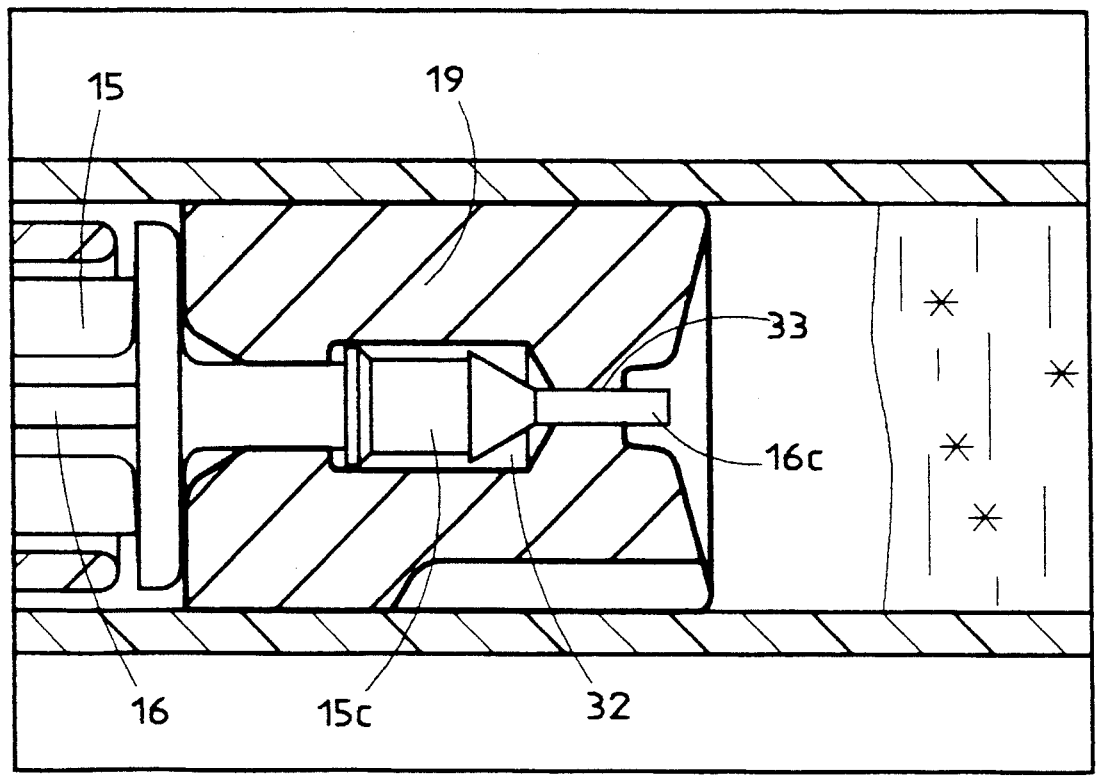
Figure 27:
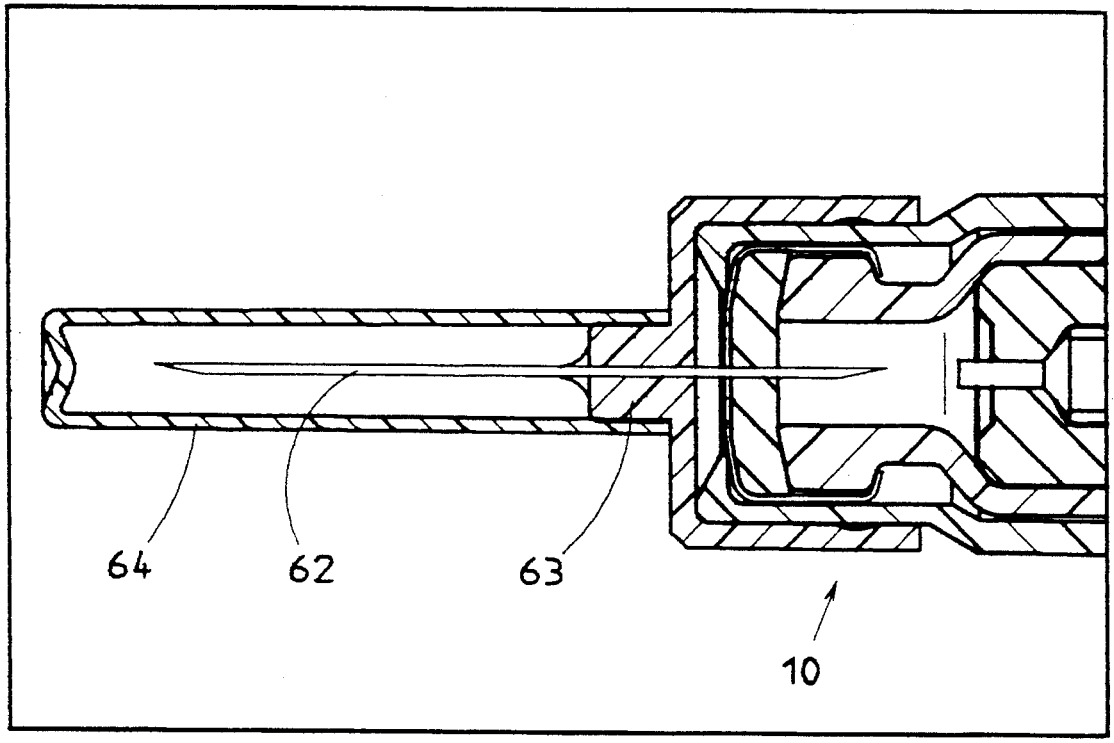
FIGS. 27 to 30 show enlarged views of adaptable device accessories in function of during use.

FIG. 26 shows the stopper-piston-dish 19 shown by FIG. 24 in a phase of putting to use. There, once again, the end 15c of conveyance shaft 15 has been pushed back inside the central groove 32 and the end 16c of conduit 16 has been pushed along the prepunched slit 33. As before, the zones of tightness and the barriers of sterility are preserved in this phase.

FIGS. 27 to 30 illustrate different accessories or peripheries intended to be linked to the device 10 with a view to specific utilizations of this device. FIG. 17 in particular is an enlarged view of the end of device 10, such as shown by FIG. 12, the needle 62 mounted upon a flange 63 is protected by a protection hood 64.

Figure 28:
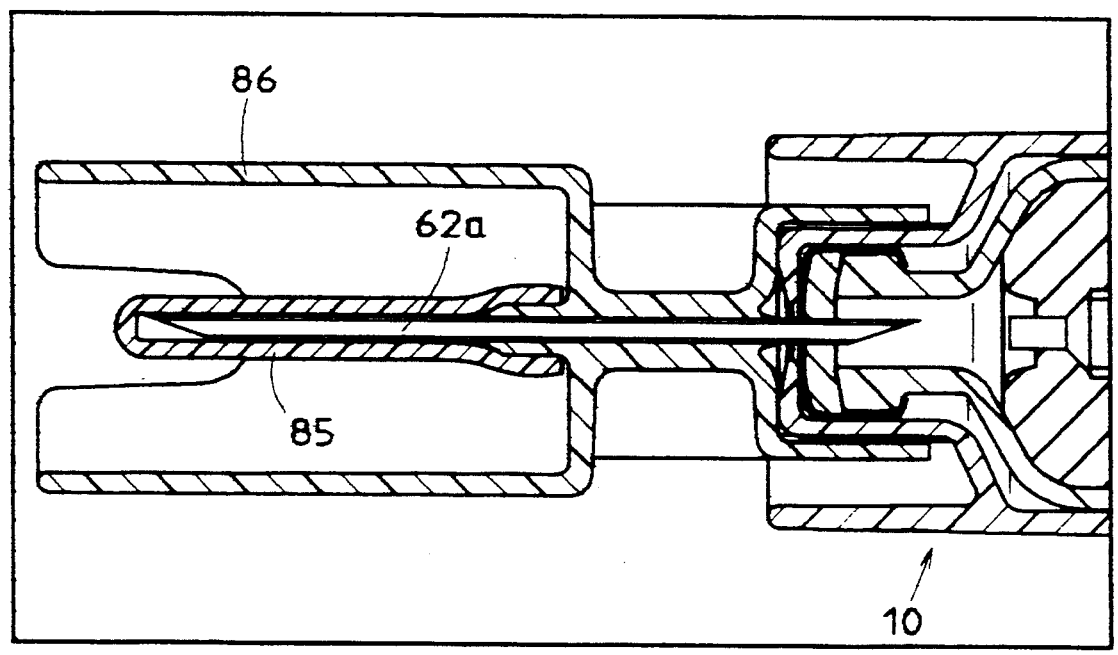

FIG. 28 shows a different form of construction in which a conveyance needle 62a is protected by a rigid guard 80 made of synthetic material. This needle 62a, besides, is concealed by a sleeve 81. This sleeve 81 has the function to avoid a nebulation of the substance in question inside the device 10 at the moment of connection of this device to a different container, such as for instance a transfusion bag, along conveyance needle 62. In effect, by reason of a light pressure existing the inside the device 10, a nebulation of the medical substance could be produced, which could be dangerous to the staff attending. This nebulation is avoided due to protection ensured by the sleeve 81, which is flexible and folds up when the conveyance needle is sunk into a suitable ferrule to the transfusion bag, then it unfolds from at the moment of withdrawal and disconnection in order to obturate the device 10.

Figure 29:
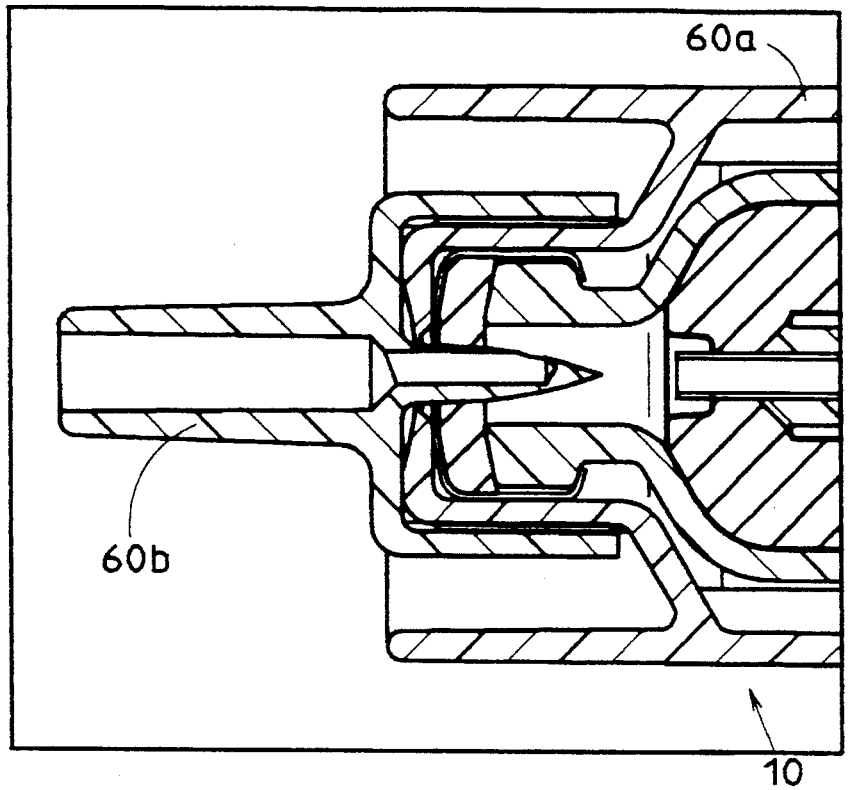

FIG. 29 shows device 10 provided with a sleeve 80a having substantially the same functions as the sleeve 60 shown by FIG. 10. Over the end of this sleeve is fitted a ferrule 60b having a shape to permit the fitting of accessories, such as a needle supports, a ferrule, etc.

Figure 30:
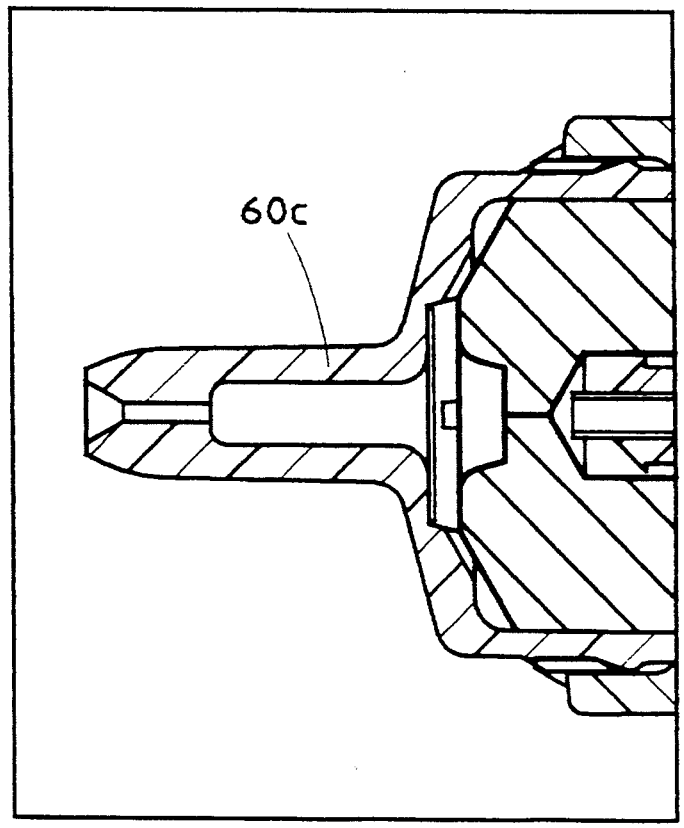

FIG. 30 is similar to FIG. 29, but the ferrule 60b has been replaced by a ferrule 60c in the shape of a male cone.

The following Figures show schematically the phases of assembly and of construction of the device 10 and its components in different stages, that is to say, when the rear container is meant to contain a lyophilisate, a liquid more or less sticky and a powder. FIG. 31 shows the rear container located in a cassette 90. It will be noted that this compressed arrangement is possible due to the cylindrical shape of this container. FIG. 32 illustrates the filling of the rear container 11 by means of a solution meant to be lyophilisated.

FIG. 33 illustrates a phase of pre-positioning the stopper-piston-dish 19.

FIG. 34 illustrates the phase of lyophilisation during which vapour and gases can escape by way of the gaps 91 arranged in the lower zone of the stopper-piston-dish 19. It will be noted that the transmission is easy due to the fiat bottom of the bottle, this enhancing the homogeneous formation of ice crystals and the almost total dessication of the lyophilisated product.

FIG. 35 illustrates the phase of tight closure of the rear container. This closure is accomplished by insertion of the stopper-piston-dish 19 by means of a button 92, which can be put directly at the top of the chamber inside which the operation is prepared.

FIG. 36 shows a phase of positioning the stopper-piston-dish 19, a position performed automatically by aspiration of this member inside the rear container in which there is a void, then mechanically in order to adjust the final position.

FIG. 37 shows the return of the filled containers into the magazine 90.

It will be noted that all these operations are accomplished by means of standard arrangements, as one utilized in the pharmaceutical industry. in the case where the active substance contained in the container 11 is a liquid and not a lyophilisate, the process is simplified until it allows only phases of filling represented by FIG. 32, of propositioning the stopper-piston-dish represented by FIG. 33 and final installation of this stopper-piston-dish, possibly by means of a suitable button which permits a de-aeration inside the container.

Figure 38:
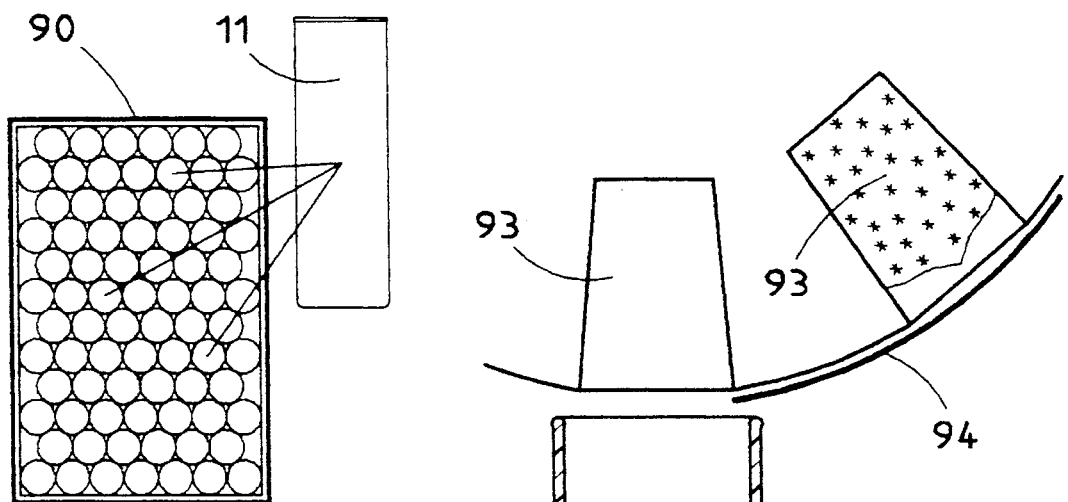
Figure 39:
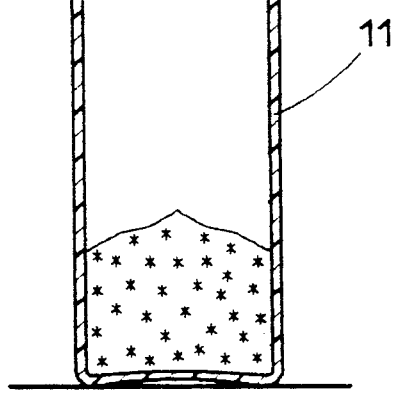
Figure 40:
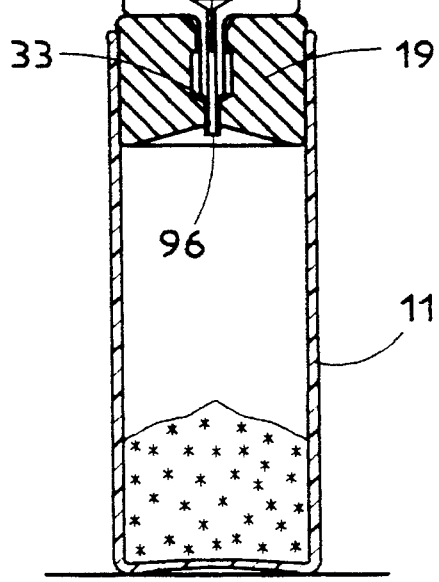
Figure 41:
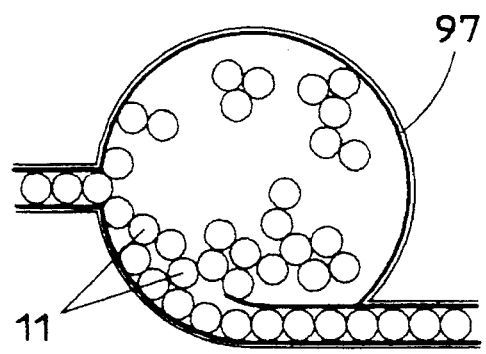
Figure 42:
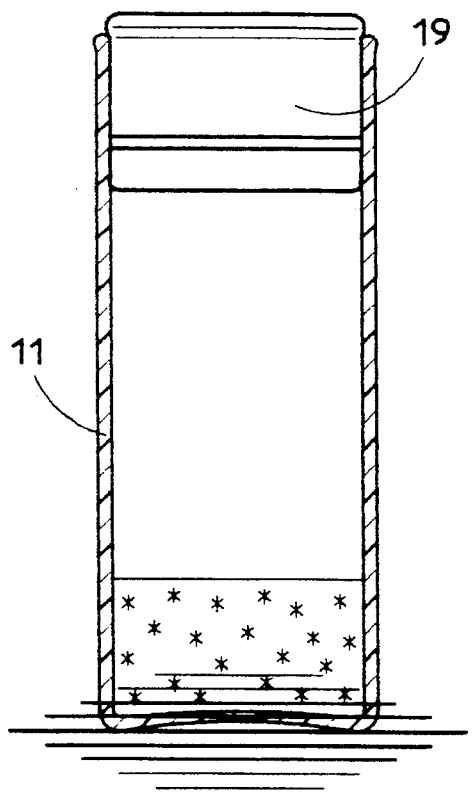

FIGS. 38 to 44 illustrate the filling of the rear container 11 with a powder. FIG. 38 shows in particular the container 11 located in a cassette 90. FIG. 39 illustrates filling of the container 11 with a dosis of powder, these doses being contained in bowls of pipe 93 mounted over an access system of guide 94 utilized in the pharmaceutical industry. FIG. 40 illustrates a phase of propositioning the stopper-piston-dish 19, accomplished by a phase of de-aeration by means of a ferrule 95. This ferrule can receive an injection-tube 96, which is passed along the slit 33 of the stopper-piston-dish. After withdrawal of this instrument, the rear containers are introduced in over the conveyance level 97 in an orderly disposition with a view to treatment as shown in FIG. 41. FIG. 42 shows the rear container with its stopper-piston-dish 19 propositioned in such a way that it rises from conveyance level 97 of FIG. 41. This phase of vibration of the powder is necessary to ensure its fixation at the bottom of the container.

Figure 43:
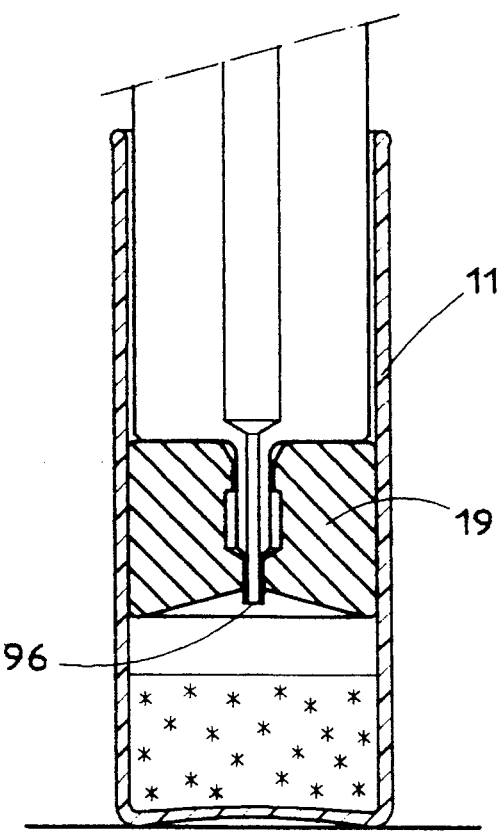
Figure 44:
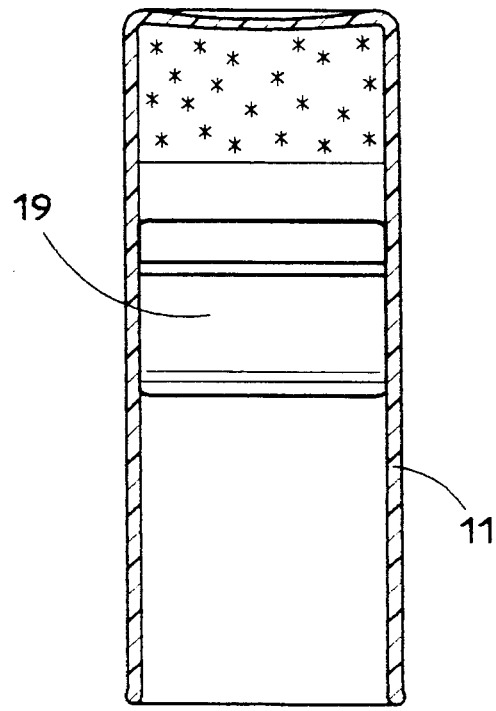

The precise positioning of the stopper-piston-dish 19 inside the rear container 11 is accomplished, as is shown in FIG. 43, by suction of gases rising over the powder along the injection-tube 96 described with reference to FIG. 40, FIG. 44 illustrates the rear container 11 with the stopper-piston-dish conveniently positioned. The powder is scraped from the walls of the container, from the time of installation of this stopper-piston-dish due to the pressure which it exerts upon these wails. Nevertheless, a phase of discontamination consisting in evacuating the residues of powder on the inner and outer sides of the rear container remains necessary.

Figure 45:
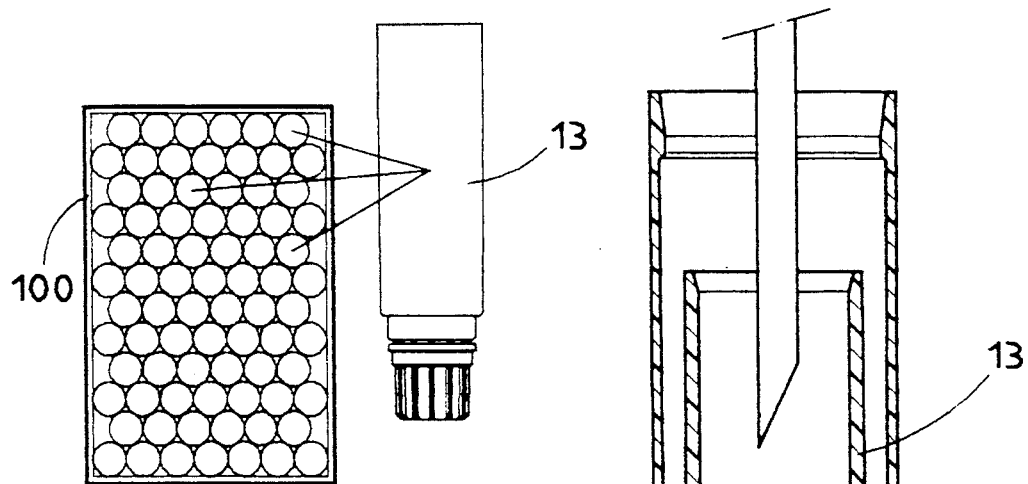
Figure 46:
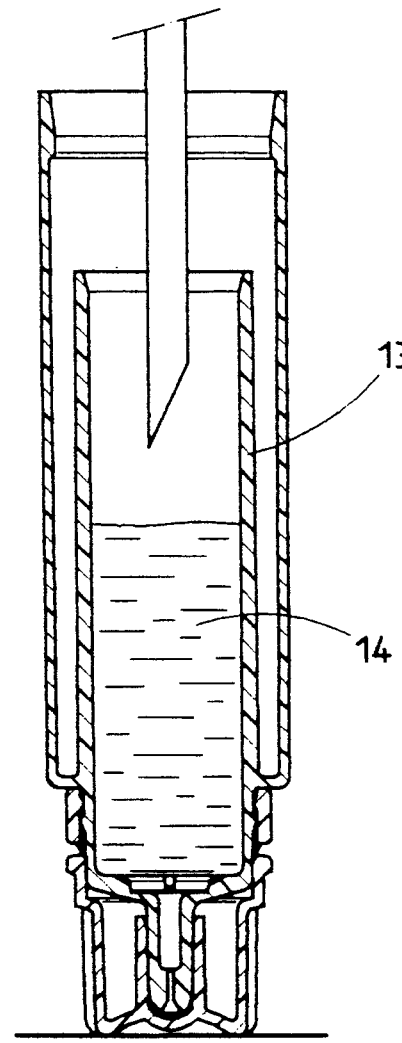
Figure 47:
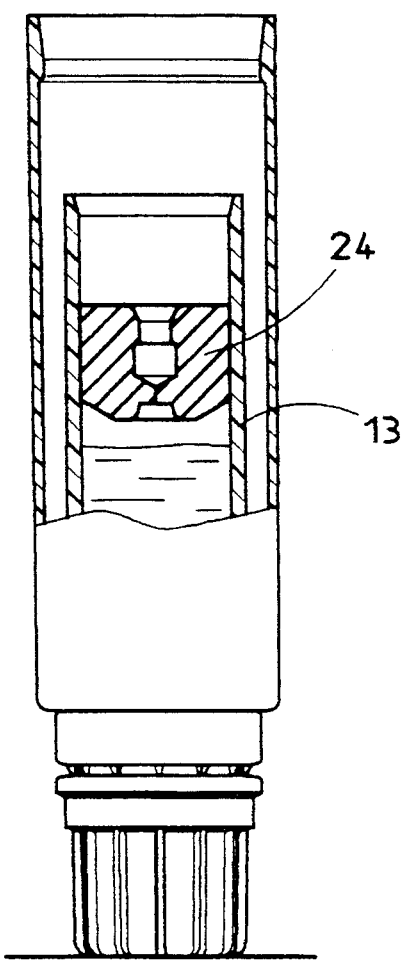
Figure 48:
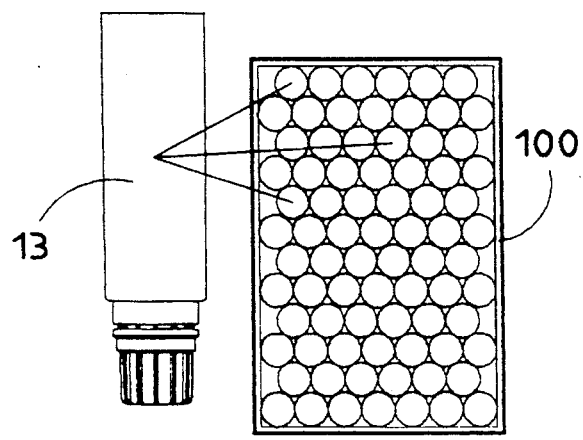

FIGS. 45 to 54 illustrate the assembly of the device 10 specifically intended for an ophtalmic application. FIG. 45 illustrates the front container 13 located in a cassette 100. This container corresponds to those which have previously been described with reference notably to FIG. 5 and to FIGS. 19 and 22. FIG. 46 illustrates the filling phase of the container 13 by means of a liquid 14 which may be a solvent or a dilutant, as has been mentioned before. FIG. 47 illustrates the installation phase of the stopper-piston-dish 24 inside the container 13. After these different steps, the containers 13 are replaced into the cassettes 100 (FIG. 48 refers). As previously, this compressed arrangement into cassette is possible only due to the fact that these containers have a cylindrical shape provided with roughnesses and notably protruding screws.

The containers 13 disposed into cassette may be charged during a more or less extended phase and possibly subjected to treatment such as for instance sterilization. This phase is illustrated by FIG. 49. FIG. 50 represents a cassette 90 in which are placed the rear containers 11. FIG. 51 illustrates the installation of the conveyance shaft 15 in the front container 13.

Figures 52, 53, 54:
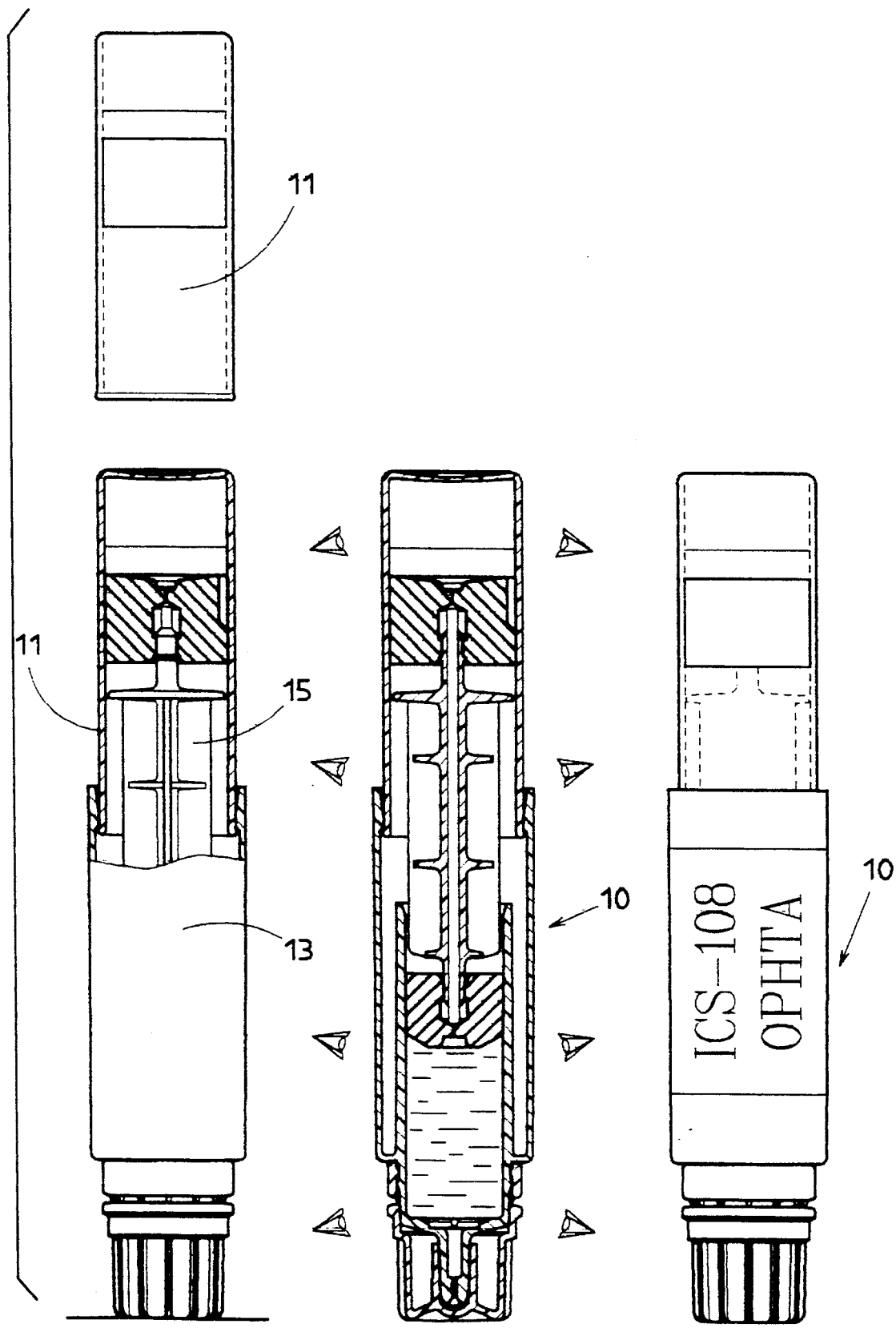

FIG. 52 illustrates the terminal assembly phase which consists of installing rear container 11 upon the conveyance shaft 15 previously/first positioned inside the front container 13.

FIG. 53 illustrates a phase of visual control of the premounted device 10. FIG. 54 illustrates the device 10 wholly assembled and controlled according to different steps specified above.

It will be noted that all these operations are possible with standard equipment mainly utilized in the pharmaceutical industry and that special machines are not needed for assembly of the different components of the device. To facilitate this assembly and a decrease the costs, the number of changes of modes of arrangement, notably the number of transitions from an orderly disposition towards a disorderly one, is limited to a minimum.

FIGS. 55 to 62 illustrate the step of preparing the front container 13 and the installation of me conveyance shaft 15. The empty container 13 is, as shown in FIG. 55, located in cassettes 100. FIG. 56 illustrates the phase of positioning the stopper-piston-dish 24 inside this container 13. FIG. 57 illustrates the filling phase of solvent or dilutant 14. FIG. 58 illustrates the éncapsulation of this container, that is to say, the installation of capsule 22. FIG. 59 illustrates the return of container 13 into the cassettes 100 with a view to instant charging or external treatments, as for instance sterilization. FIG. 60 illustrates the installation of containers 13 charged in cassettes 100 after possible sterilization treatments or similarly inside a sleeve 60 such as represented by FIG. 10. These sleeves 60 themselves are set apart inside the cassettes 110, where they are charged in view of this assembly. FIG. 61 represents the installation of the conveyance shaft 15 on the front container 13 first mounted inside the sleeve 60. FIG. 62 represents the installation of rear container 11 on the other end of the conveyance shaft 15 first assembled as shown in FIG. 61.

The assembly is made by standard means which are utilized currently in the pharmaceutical industry and which do not necessitate special equipment.

Besides, most of the components and notably the rear and front containers, the same as the sleeve, in which is disposed the front container, are located in the cassettes, which reduces or suppresses the number of transitions from an orderly state towards a disorderly one.

I claim:

1. Device for the preparation of at least one of a solution, a suspension and an emulsion from an active medicinal substance comprising:

a first component being in at least one of a powder form, a lyophilisate, a liquid, and a paste;

a second component being at least one of a dilutant and a liquid solvent;

a first container (11) for storing said first component, said first container being closed at a first end (17);

a second container (13) for storing said second component;

a first stopper piston dish (19) at a second end of said first container (11), said first stopper piston dish (19) being axially movable within said first container (11);

a second stopper piston dish (24) at a first end of said second container (13), said second stopper piston dish (24) being axially movable within said second container (13);

a conveyance shaft (15) connecting said first and second stopper piston dishes (19, 24), said conveyance shaft (15) ensuring a rigid, tight, and sterile connection between said stopper piston dishes (19, 24) when said device is in a charging position, and defining a tight and sterile channel of communication between said containers (11, 13) when said device is in a use position, said use position being a position wherein said first stopper piston dish (19) of said first container (11) is at a higher level than said second stopper piston dish (24) of said second container (13);

at least one end of said conveyance shaft (15) being shaped in a plane substantially perpendicular to a longitudinal axis of said conveyance shaft;

a first slit (33) in a central zone of said first stopper piston dish (19), said first slit (33) being strongly compressed and tightly closed when said device is in said charging position, said first slit (33) being opened when a first end of said conveyance shaft (15) is introduced into said first slit (33) when said device is in said use position; and a second slit (31) in a central zone of said second stopper piston dish (24), said second slit (31) being strongly compressed and tightly closed when said device is in said charging position, said second slit (31) being opened when a second end of said conveyance shaft (15) is introduced into said second slit (31) when said device is in said use position.

2. Device according to claim 1 comprising a sleeve (60) containing said second container (13) and at least partially containing said first container (11).

3. Device according to claim 2 comprising:

a cup (70) linked to said sleeve (60); and a mechanism (71) linked to said sleeve (60) for application of multiple doses.

4. Device according to claim 2 wherein said sleeve (60) is integrally formed with said second container (13).

5. Device according to claim 2 comprising a ferrule for said sleeve (60), said ferrule comprising at least one of an ophthalmic drops applicator and a nasal vaporizer, integrally formed in said second container (13).

6. Device according to claim 2 comprising:

a first tubular element (42), within said sleeve (60), containing said first container (11); and a second tubular element (40), within said sleeve (60), containing said second container (13), said first and second tubular elements being fitted one into another.

7. Device according to claim 6 comprising:

a plurality of catches (43) on said first tubular element (42);

at least two tongue shaped strips (44) on said second tubular element (40), being arranged to cooperate with said catches (43).

8. Device according to claim 1 comprising:

a first central groove (32) in said first stopper piston dish (19);

a second central groove (26) in said second stopper piston dish (24); and means for tight and sterile coupling of said conveyance shaft (15) to said stopper piston dishes (19, 24).

9. Device according to claim 1 comprising a plurality of stop abutments on said conveyance shaft (15), each said stopper piston dish (19, 24) has first surfaces, and said stop abutments support said first surfaces of said stopper piston dishes (19, 24) when said device is in said use position.

10. Device according to claim 1 wherein said stopper piston dishes (19, 24) support an inner side of said containers (11, 13) such that said containers (11, 13) is charged and handled independently, ensuring a tight and sterile closure of said containers (11, 13).

11. Device according to claim 1 wherein said conveyance shaft (15) ensures a tight, rigid and sterile connection of said stopper piston dishes (19, 24), said stopper piston dishes (19, 24) being respectively located in said first container (11) and said second container (13).

12. Device according to claim 1 wherein said second container (13) is adapted to receive a plurality of different ferrules and applicators for functioning in various therapeutical uses.

* * * * *